(12) United States Patent
Macpherson et al.

(10) Patent No.: US 10,790,041 B2
(45) Date of Patent: Sep. 29, 2020

(54) METHOD FOR ANALYZING AND DISPLAYING GENETIC INFORMATION BETWEEN FAMILY MEMBERS

(71) Applicant: 23andMe, Inc., Mountain View, CA (US)

(72) Inventors: John Michael Macpherson, Mountain View, CA (US); Joanna Sim, Mountain View, CA (US); Brian Thomas Naughton, Mountain View, CA (US); Michael Polcari, San Francisco, CA (US)

(73) Assignee: 23andMe, Inc., Sunnyvale, CA (US)

( * ) Notice: Subject to any disclaimer, the term of this patent is extended or adjusted under 35 U.S.C. 154(b) by 361 days.

(21) Appl. No.: 15/428,968

(22) Filed: Feb. 9, 2017

(65) Prior Publication Data

US 2017/0329924 A1    Nov. 16, 2017

Related U.S. Application Data

(63) Continuation of application No. 13/587,276, filed on Aug. 16, 2012, now abandoned.
(Continued)

(51) Int. Cl.
*G16H 50/30* (2018.01)
*G16B 20/00* (2019.01)
(Continued)

(52) U.S. Cl.
CPC .............. *G16B 20/00* (2019.02); *G16B 50/30* (2019.02); *G16H 50/30* (2018.01); *G16H 50/70* (2018.01); *G16B 40/00* (2019.02)

(58) Field of Classification Search
CPC .......... G06F 17/30; G06Q 50/01; G16B 50/30
(Continued)

(56) References Cited

U.S. PATENT DOCUMENTS

| 6,570,567 | B1 | 5/2003 | Eaton |
| 6,760,731 | B2 | 7/2004 | Huff |

(Continued)

FOREIGN PATENT DOCUMENTS

WO    WO-2008135986 A2 *  11/2008    ............. G16B 20/00

OTHER PUBLICATIONS

A method for detecting IBD regions simultaneously in multiple individuals, Ida Multke et al., teh bioinformetics centre, university of Kopenhagen, 2011 (Year: 2011).*
(Continued)

*Primary Examiner* — Dilek B Cobanoglu
(74) *Attorney, Agent, or Firm* — Weaver Austin Villeneuve & Sampson LLP; David K. Buckingham

(57) ABSTRACT

A technique of using collaborative family medical history (CFMH) to estimate disease risk includes establishing CFMH information of a user and a plurality of relatives of the user, the CFMH information including genetic information of at least some of the family members, genetic information of the user, or both. It further includes analyzing the CFMH information, including the genetic information. It further includes determining a potential risk condition of the user and a potential risk condition of at least a family member based on the CFMH information. It also includes outputting the potential risk condition of the user and the potential risk condition of the at least one family member.

19 Claims, 15 Drawing Sheets

Related U.S. Application Data

(60) Provisional application No. 61/524,578, filed on Aug. 17, 2011.

(51) Int. Cl.
  *G16H 50/70* (2018.01)
  *G16B 50/30* (2019.01)
  *G16B 40/00* (2019.01)

(58) Field of Classification Search
  USPC .............................................. 705/2; 707/803
  See application file for complete search history.

(56) References Cited

U.S. PATENT DOCUMENTS

| | | | |
|---|---|---|---|
| 8,024,128 B2* | 9/2011 | Rabinowitz ............ | G16B 40/00 702/19 |
| 8,156,158 B2* | 4/2012 | Rolls .................. | G06F 19/3443 707/803 |
| 8,224,862 B2* | 7/2012 | Sacks .................... | G06Q 10/10 707/797 |
| 8,275,635 B2 | 9/2012 | Stivoric et al. | |
| 9,330,418 B2* | 5/2016 | Hulet .................... | G06Q 50/01 |
| 2002/0128860 A1 | 9/2002 | Leveque et al. | |
| 2004/0134440 A1 | 7/2004 | Da et al. | |
| 2005/0074795 A1 | 4/2005 | Hoffman et al. | |
| 2006/0136143 A1 | 6/2006 | Avinash et al. | |
| 2007/0026603 A1 | 2/2007 | Lee et al. | |
| 2007/0027636 A1 | 2/2007 | Rabinowitz | |
| 2008/0133270 A1 | 6/2008 | Michelson et al. | |
| 2008/0228768 A1 | 9/2008 | Kenedy et al. | |
| 2010/0022406 A1* | 1/2010 | Srinivasan ............ | G06Q 30/06 506/9 |
| 2010/0199222 A1 | 8/2010 | Kranik et al. | |
| 2013/0149707 A1* | 6/2013 | Sorenson ............... | G16B 30/00 435/6.12 |

OTHER PUBLICATIONS

Google patents search, Feb. 5, 2020 (Year: 2020).*
Google patents search, Feb. 4, 2020 (Year: 2020).*
IP.com patents search, May 18, 2020 (Year: 2020).*
IP.com NPL search, May 18, 2020 (Year: 2020).*
Google patents search, May 8, 2015.
"A method for detecting IBD regions simultaneously in multiple individuals-with applications to disease genetics" by Ida Moltke, V Anders Albrechtsen, Thomas v.O. Hansen, Finn C. Nielsen and Rasmus Nielsen, The Bioinformatics Centre, Department of Biology, University of Copenhagen, 2200 Copenhagen, Denmark, www.genome.org.
U.S. Office Action dated Mar. 21, 2014 issued in U.S. Appl. No. 13/587,276.
U.S. Office Action dated Sep. 3, 2014 issued in U.S. Appl. No. 13/587,276.
U.S. Final Office Action dated May 14, 2015 issued in U.S. Appl. No. 13/587,276.
U.S. Office Action dated Jan. 7, 2016 issued in U.S. Appl. No. 13/587,276.
U.S. Final Office Action dated Oct. 13, 2016 issued in U.S. Appl. No. 13/587,276.

* cited by examiner

FIG. 5A

| Member ID | Genetic Information | | Family History Information | | Environmental Information | | Has PD? |
|---|---|---|---|---|---|---|---|
| | SNP rs12778775 risk allele | ... | Mother has PD? | ... | Exposed to pesticides at work? | ... | |
| 0001 | yes | ... | yes | ... | no | ... | yes |
| 0002 | no | ... | no | ... | yes | ... | yes |
| ... | ... | ... | ... | ... | ... | ... | ... |
| 2999 | no | ... | no | ... | yes | ... | no |
| 3000 | yes | ... | no | ... | no | ... | no |
| ... | ... | ... | ... | ... | ... | ... | ... |
| 4000 | no | ... | no | ... | no | ... | yes |
| ... | ... | ... | ... | ... | ... | ... | ... |

FIG. 11

METHOD FOR ANALYZING AND DISPLAYING GENETIC INFORMATION BETWEEN FAMILY MEMBERS

CROSS REFERENCE TO RELATED APPLICATIONS

This application is a continuation of U.S. patent application Ser. No. 13/587,276, filed Aug. 16, 2012, entitled COLLABORATIVE FAMILY MEDICAL HISTORY ON A PERSONAL GENETICS SERVICE PLATFORM by Macpherson et al., which claims the benefit of U.S. Provisional Application No. 61/524,578, filed Aug. 17, 2011, entitled COLLABORATIVE MEDICAL HISTORY by Macpherson et al., which applications are herein incorporated by reference in their entirety for all purposes.

BACKGROUND OF THE INVENTION

Family history information can improve the accuracy of estimating disease risk. For example, if it is known that a person's close relative had a certain disease that is typically attributed to a specific gene, it is possible that the person's risk of getting that disease would increase. Many diseases, however, are not necessarily linked to a single genetic factor, and therefore it is difficult to tell whether the presence of the disease in the family is due to genetic factors or other reasons such as environmental information or life style. Moreover, a person's knowledge about her own family's medical history can be limited, which means that predictions of one's own disease risk are typically based on limited data and can be inaccurate.

BRIEF DESCRIPTION OF THE DRAWINGS

Various embodiments of the invention are disclosed in the following detailed description and the accompanying drawings.

FIG. 5A is a diagram illustrating an embodiment of an initial user interface display for starting a user's health profile.

FIG. 11 is a diagram illustrating an embodiment of a member information table used to train and validate the model.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Using collaborative family medical history (CFMH) to estimate disease risk is described. In some embodiments, on a platform (such as the personal genetic services platform offered by 23andMe, Inc.) where users have the options to test for genetic information and connect with each other, a family tree is populated by a user and the user's family members. The conditions associated with various family members are entered collaboratively by the user and her family members. Based on the CFMH information as well as genetic information, estimated disease risks are determined and presented to the user and/or her family members.

Figure 1:
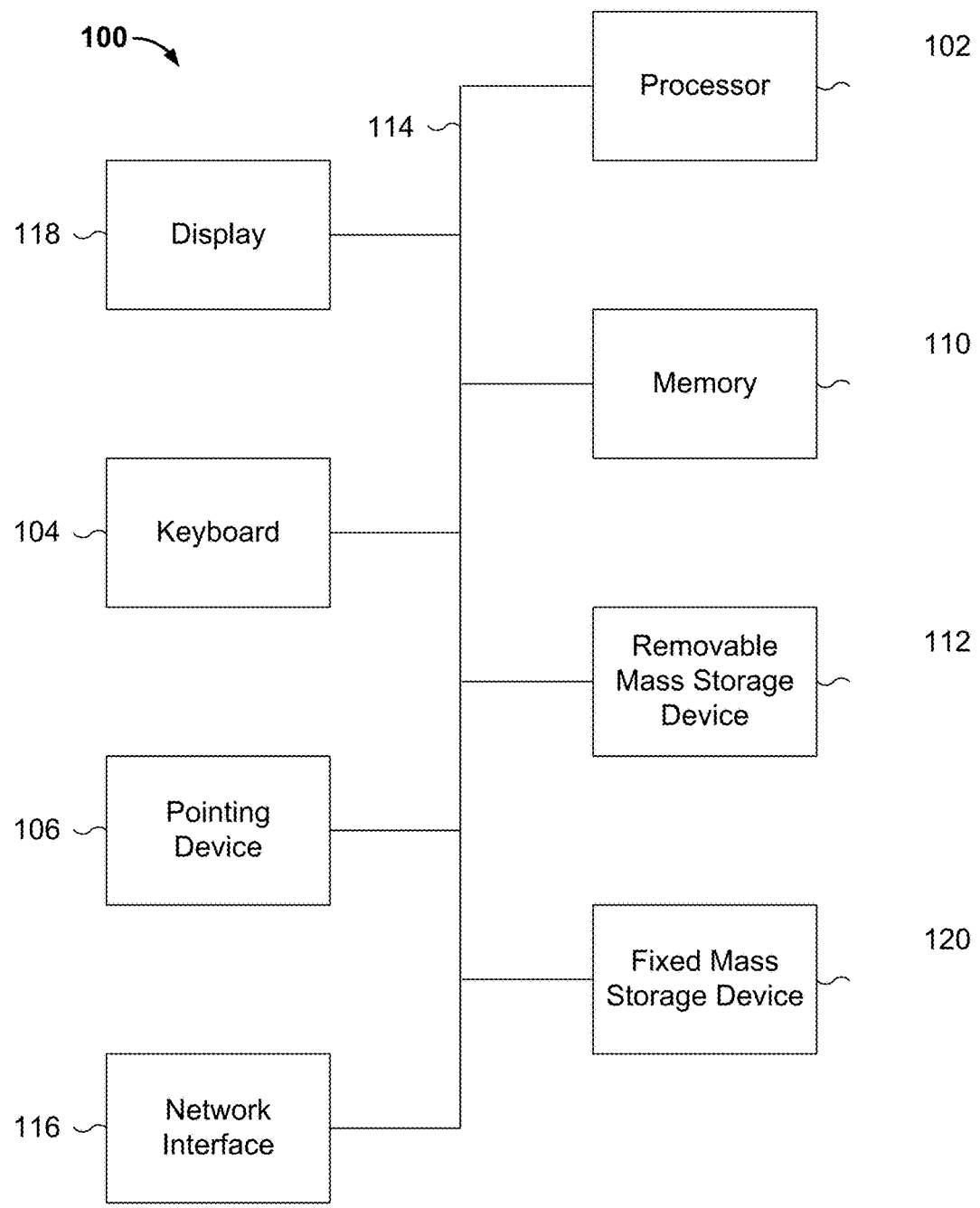
FIG. 1 is a functional diagram illustrating an embodiment of a programmed computer system for using collaborative family medical history (CFMH) to estimate disease risk.

FIG. 1 is a functional diagram illustrating an embodiment of a programmed computer system for using collaborative family medical history (CFMH) to estimate disease risk. As will be apparent, other computer system architectures and configurations can be used to estimate disease risk using collaborative family medical history (CFMH). Computer system 100, which includes various subsystems as described below, includes at least one microprocessor subsystem (also referred to as a processor or a central processing unit (CPU)) 102. For example, processor 102 can be implemented by a single-chip processor or by multiple processors. In some embodiments, processor 102 is a general purpose digital processor that controls the operation of computer system 100. Using instructions retrieved from memory 110, processor 102 controls the reception and manipulation of input data, and the output and display of data on output devices (e.g., display 118). In some embodiments, processor 102 includes and/or is used to estimate disease risk using collaborative family medical history.

Processor 102 is coupled bi-directionally with memory 110, which can include a first primary storage, typically a random access memory (RAM), and a second primary storage area, typically a read-only memory (ROM). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor 102. Also as is well known in the art, primary storage typically includes basic operating instructions, program code, data and objects used by processor 102 to perform its functions (e.g., programmed instructions). For example, memory 110 can include any suitable computer-readable storage media, described below, depending on whether, for example, data access needs to be bi-directional or uni-directional. For example, processor 102 can also directly and very rapidly retrieve and store frequently needed data in a cache memory (not shown).

A removable mass storage device 112 provides additional data storage capacity for computer system 100, and is coupled either bi-directionally (read/write) or uni-directionally (read only) to processor 102. For example, storage 112 can also include computer-readable media such as magnetic tape, flash memory, PC-CARDS, portable mass storage devices, holographic storage devices, and other storage devices. A fixed mass storage 120 can also, for example, provide additional data storage capacity. The most common example of mass storage 120 is a hard disk drive. Mass storage 112, 120 generally store additional programming instructions, data, and the like that typically are not in active use by processor 102. It will be appreciated that the information retained within mass storage 112 and 120 can be incorporated, if needed, in standard fashion as part of memory 110 (e.g., RAM) as virtual memory.

In addition to providing processor 102 access to storage subsystems, bus 114 can also be used to provide access to other subsystems and devices. As shown, these can include a display monitor 118, a network interface 116, a keyboard 104, and a pointing device 106, as well as an auxiliary input/output device interface, a sound card, speakers, and other subsystems as needed. For example, the pointing device 106 can be a mouse, stylus, track ball, or tablet, and is useful for interacting with a graphical user interface.

The network interface 116 allows processor 102 to be coupled to another computer, computer network, or telecommunications network using a network connection as shown. For example, through the network interface 116, the processor 102 can receive information (e.g., data objects or program instructions) from another network or output information to another network in the course of performing method/process steps. Information, often represented as a sequence of instructions to be executed on a processor, can be received from and outputted to another network. An interface card or similar device and appropriate software implemented by (e.g., executed/performed on) processor 102 can be used to connect the computer system 100 to an external network and transfer data according to standard protocols. For example, various process embodiments disclosed herein can be executed on processor 102, or can be performed across a network such as the Internet, intranet networks, or local area networks, in conjunction with a remote processor that shares a portion of the processing. Additional mass storage devices (not shown) can also be connected to processor 102 through network interface 116.

An auxiliary I/O device interface (not shown) can be used in conjunction with computer system 100. The auxiliary I/O device interface can include general and customized interfaces that allow processor 102 to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a non-transitory computer readable medium that includes program code for performing various computer-implemented operations. The computer-readable medium is any data storage device that can store data which can thereafter be read by a computer system. Examples of non-transitory computer-readable media include, but are not limited to, all the media mentioned above: magnetic media such as hard disks, floppy disks, and magnetic tape; optical media such as CD-ROM disks; magneto-optical media such as optical disks; and specially configured hardware devices such as application-specific integrated circuits (ASICs), programmable logic devices (PLDs), and ROM and RAM devices. Examples of program code include both machine code, as produced, for example, by a compiler, or files containing higher level code (e.g., script) that can be executed using an interpreter.

The computer system shown in FIG. 1 is but an example of a computer system suitable for use with the various embodiments disclosed herein. Other computer systems suitable for such use can include additional or fewer subsystems. In addition, bus 114 is illustrative of any interconnection scheme serving to link the subsystems. Other computer architectures having different configurations of subsystems can also be utilized.

Figure 2:
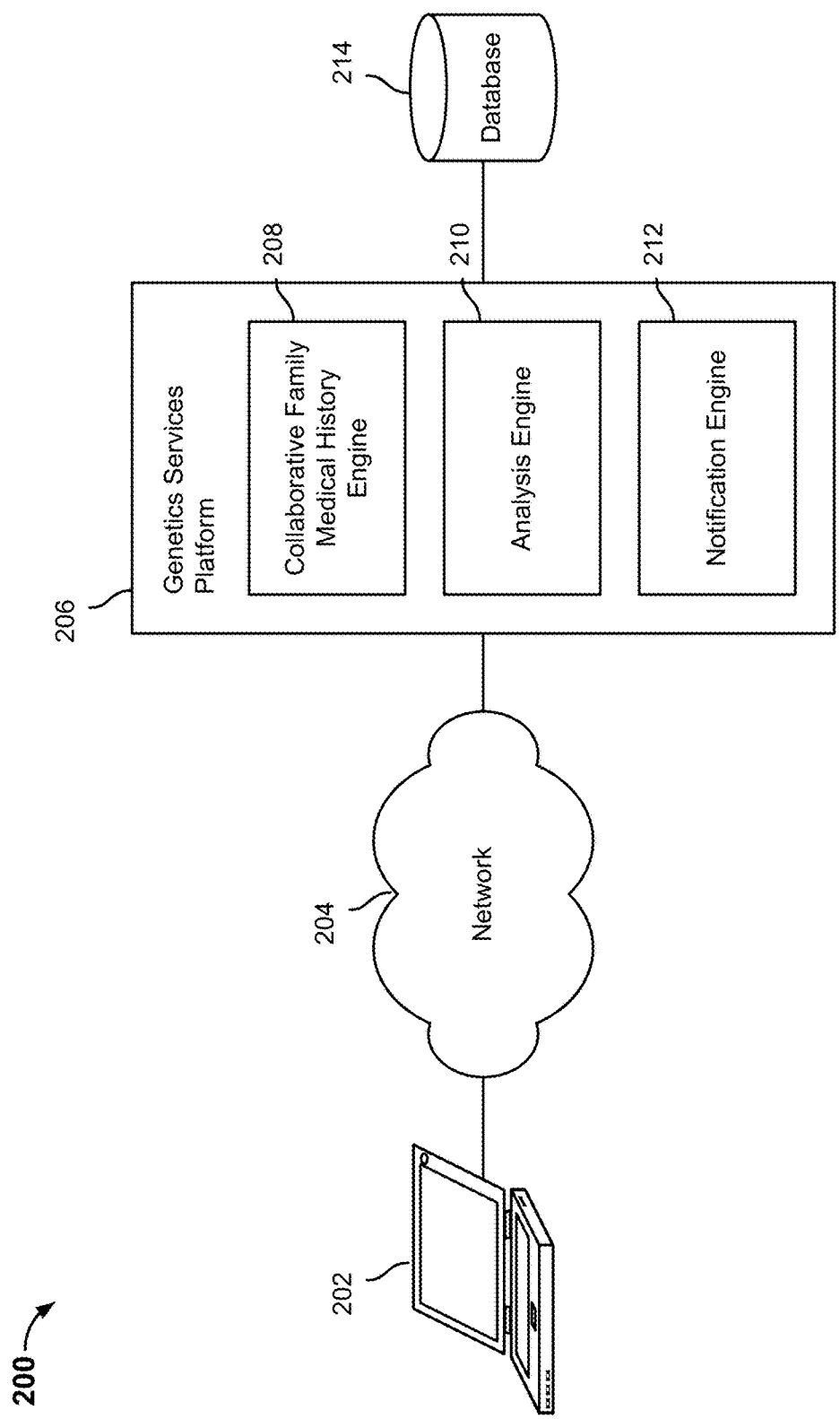
FIG. 2 is a system diagram illustrating an embodiment of a system for using CFMH to estimate disease risk.

FIG. 2 is a system diagram illustrating an embodiment of a system for using CFMH to estimate disease risk. In this example, a user uses a client device 202 to communicate with a personal genetics services platform via a network 204. Examples of device 202 include a laptop computer, a desktop computer, a smart phone, a mobile device, a tablet device or any other computing device. The personal genetic services platform can be a networked platform (e.g., a server or cloud-based platform, a peer-to-peer platform, etc.) that supports various applications. For example, embodiments of the platform provide users with access to their personal genetic information (e.g., genetic sequence information and/or genotype information obtained by assaying genetic materials such as blood or saliva samples) as well as other information such as family medical history, allow users to connect with each other, share their information, and collaborate on family medical history information. As shown, device 202 is configured to communicate with the personal genetics services platform 206, which includes CFMH engine 208, analysis engine 210, notification engine 212, and database 214. In various embodiments, an application such as a web browser or a client application is installed at device 202 to enable communication with the platform.

In this example, a collaborative family medical history (CFMH) engine 208 is used to establish a family tree that is populated by a user and family members invited by the user. The user and the user's family members can then collaborate on entering information about the family members and their relationships, family history of their family members (e.g., disease history of relatives), environment information (e.g., smoking habits, diet, exposure to toxins, etc.), as well as phenotype data (e.g., other concurrent diseases/conditions). The family history and environmental information can be stored in database 214 or any other appropriate storage unit. DNA samples (e.g., saliva, blood, etc.) can be collected from genotyped individuals and analyzed using DNA microarray or other appropriate techniques. The genetic information is also stored in a database that may be the same as or separate from database 214. In various embodiments, the genetic information includes genome sequences, genotype DNA information such as Single Nucleotide Polymorphisms (SNPs), Short Tandem Repeats (STRs), and Copy-Number Variants (CNVs), as well as any other appropriate representations of the subscriber's genes. Additional genetic information can be optionally stored to facilitate the prediction process. For example, genetic information that is inferred rather than directly obtained by assaying DNA samples (such as inferences made based on identical by descent regions) can be stored in the database.

An analysis engine 210 is used to analyze CFMH information (such as the information collected by CFMH engine 208) as well as genetic information (e.g., DNA information of the users) and environmental information. Based on the results of analysis performed by analysis engine 210, notification engine 212 can provide notifications/alerts to some or all members of the family (e.g., estimated disease risks for some or all of the family members).

The CFMH engine, prediction engine, and notification engine described above can be implemented as software components executing on one or more general purpose processors, as hardware such as programmable logic devices and/or Application Specific Integrated Circuits designed to perform certain functions, or a combination thereof. In some embodiments, these modules can be embodied by a form of software products which can be stored in a nonvolatile storage medium (such as optical disk, flash storage device, mobile hard disk, etc.), including number of instructions for making a computer device (such as personal computers, servers, network equipment, etc.) implement the methods described in the embodiments of the present invention. The modules may be implemented on a single device or distributed across multiple devices. The functions of the modules may be merged into one another or further split into multiple sub-modules.

Figure 3:
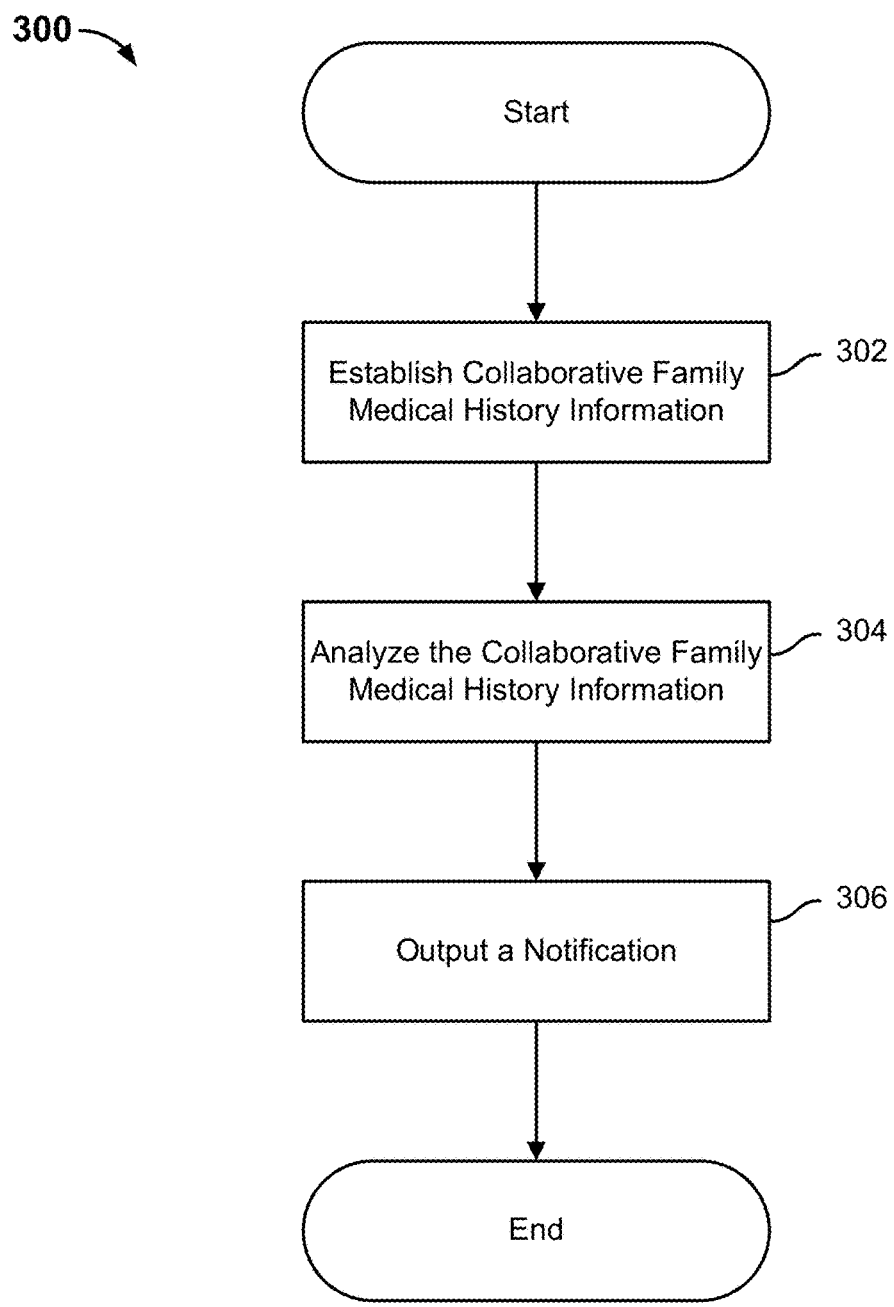
FIG. 3 is a flow diagram illustrating an embodiment of a process for using CFMH to estimate disease risk.

FIG. 3 is a flow diagram illustrating an embodiment of a process for using CFMH to estimate disease risk. Process 300 may be implemented on a system such as 200 of FIG. 2. The process begins at 302 when collaborative family medical history (CFMH) information is established. As will be described in greater detail below, in some embodiments, establishing CFMH information includes establishing a CFMH tree, inviting family members, and collaborating on the CFMH tree.

At 304, the established CFMH information (which includes non-genetic information such as environmental information and stored genetic information) is analyzed. In some embodiments, the analysis includes determining a potential risk condition (e.g., for breast cancer, type II diabetes, Parkinson's disease, etc.) based on the CFMH information (which includes environmental and genetic information). In some embodiments, the potential risk estimate for at least some or all of the family members included in the CFMH is determined when performing the analysis. A variety of analysis techniques can be used and are described in greater detail below.

In some embodiments, based on the family history information, or in response to the addition/updating of family history information, the disease risks of the family members in the tree are computed using a rule-based technique, such as the technique described in "Family History: A Comprehensive Genetic Risk Assessment Method for the Chronic Conditions of Adulthood" by Scheuner et al., Am J Med Genet, 1997. The technique places each individual in one of several risk "buckets" based on the family medical history based on a set of rules. In some embodiments, three risk buckets corresponding to substantially increased, moderately increased, and typical risk levels are used. In some embodiments, risk buckets such as high, moderate, or average levels can be used. Other labels may be used in other embodiments. For example, a rule can specify that an individual having a "first-degree" relative (e.g., a parent or sibling) with an early onset of a disease (e.g., before the age of 50) places the individual in the substantially increased risk bucket.

In some embodiments, analyzing the information includes generating a phenotype prediction. Phenotypes that can be predicted include disease as well as non-disease related traits, such as height, weight, body mass index (BMI), cholesterol levels, etc. The types of predictions include but are not limited to the probability of a disease occurring over the course of an individual's lifetime, the probability of a disease occurring within a specific time frame, the probability that the individual currently has the disease, estimates of the value of a quantitative measurement, or estimates of the distribution of likely measurements. Details of generating phenotype predictions are described below in connection with FIGS. 10-12.

In some embodiments, analyzing the information includes determining and using "Identical by Descent" (IBD) information. Because of recombination and independent assortments of chromosomes, the autosomal DNA and X chromosome DNA (collectively referred to as recombining DNA) from the parents is shuffled at the next generation, with small amounts of mutation. Thus, only relatives will share long stretches of genome regions where their recombining DNA is completely or nearly identical. Such regions are referred to as "Identical by Descent" (IBD) regions because they arose from the same DNA sequences in an earlier generation. In some embodiments, individuals in the database that share a variant-overlapping IBD region with the proband (an individual being studied) are identified. A variant-overlapping IBD region is a DNA segment that corresponds to an IBD region, and that overlaps the location where the genetic variant is found. Details of IBD information and how to determine IBD information are described below in connection with FIG. 13.

Using IBD, an individual's genetic information may be inferred if the genetic information of at least one relative of the individual is available. For example, if an individual's cousin has breast cancer and has found by genotyping or sequencing to have a BRCA mutation (a mutation in the genes BRCA1 or BRCA2), the individual would have a 1 in 8 chance of sharing an IBD region with their cousin that overlaps the location of the BRCA mutation. Absent further knowledge about the genetic information of the individual, the fact that the cousin has the BRCA mutation increases the probability of the individual having the same mutation as the cousin, which would in turn increase the individual's risk for breast cancer (e.g., individual's risk may increase by a certain percentage). If the individual has been genotyped and it is determined that the individual and the cousin share an IBD region that overlaps the BRCA gene, then it can be determined that, even without sequencing the individual's DNA specifically for the BRCA gene, the individual would also have the same BRCA mutation as the cousin (i.e., the individual's risk of breast cancer is greatly increased due to the presence of the BRCA mutation). If, however, the individual and the cousin do not share an IBD region that overlaps the BRCA gene, then the individual's risk of breast cancer does not increase as a result of the presence of the BRCA mutation in the cousin.

In some embodiments, in response to edits to one or more family members' information, analysis pertaining to some or all family members of the CFMH is performed. For example, when one family member's information is updated (e.g., edited to indicate that she has breast cancer or updated based on newly obtained DNA sequence information that indicates that her genetic information includes a BRCA mutation), the change may have an impact on the predicted outcomes/risk assessments of all family members included in the CFMH, not just of the family member whose information has been annotated. Thus, a potential risk condition of a user and of at least some of the family members may be determined based on analysis of the CFMH, genetic, and/or environmental information.

At 306, a notification is outputted. As will be described in more detail below, in some embodiments, outputting a notification includes receiving analysis results and notification criteria/rules and outputting a notification to some or all family members included in a collaborative family medical history (CFMH). The notification can be sent as an email, a message to the user's account on the platform, or other forms of communication.

Figure 4:
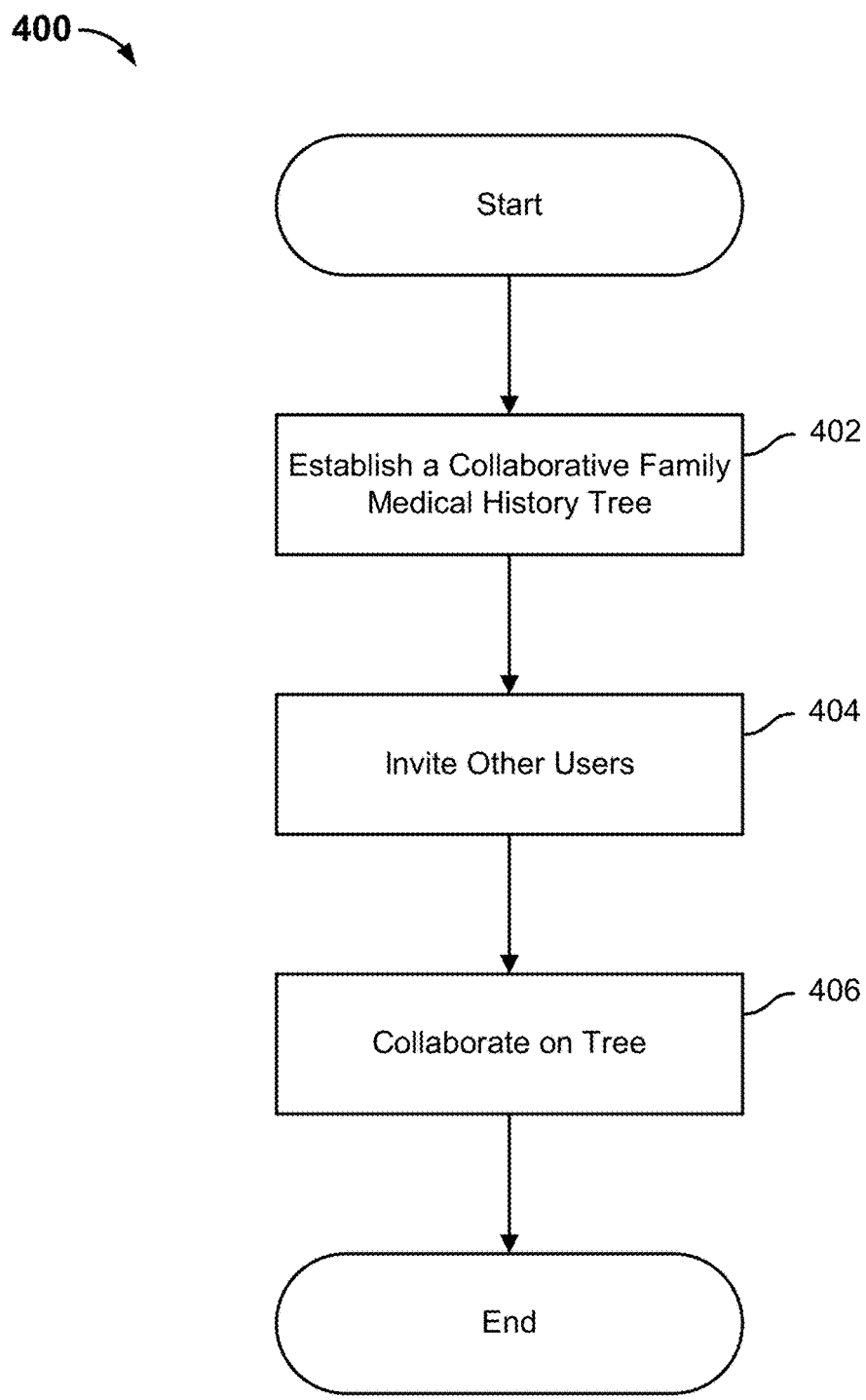
FIG. 4 is a flow diagram illustrating an embodiment of a process for establishing a collaborative family medical history.

FIG. 4 is a flow diagram illustrating an embodiment of a process for establishing a collaborative family medical history. In some embodiments, process 400 of FIG. 4 is used to implement process step 302 of FIG. 3. In some embodiments, process 400 is executed by CFMH engine 208 of FIG. 2. The process begins at 402 when a collaborative family medical history (CFMH) tree is established.

Figure 5A:
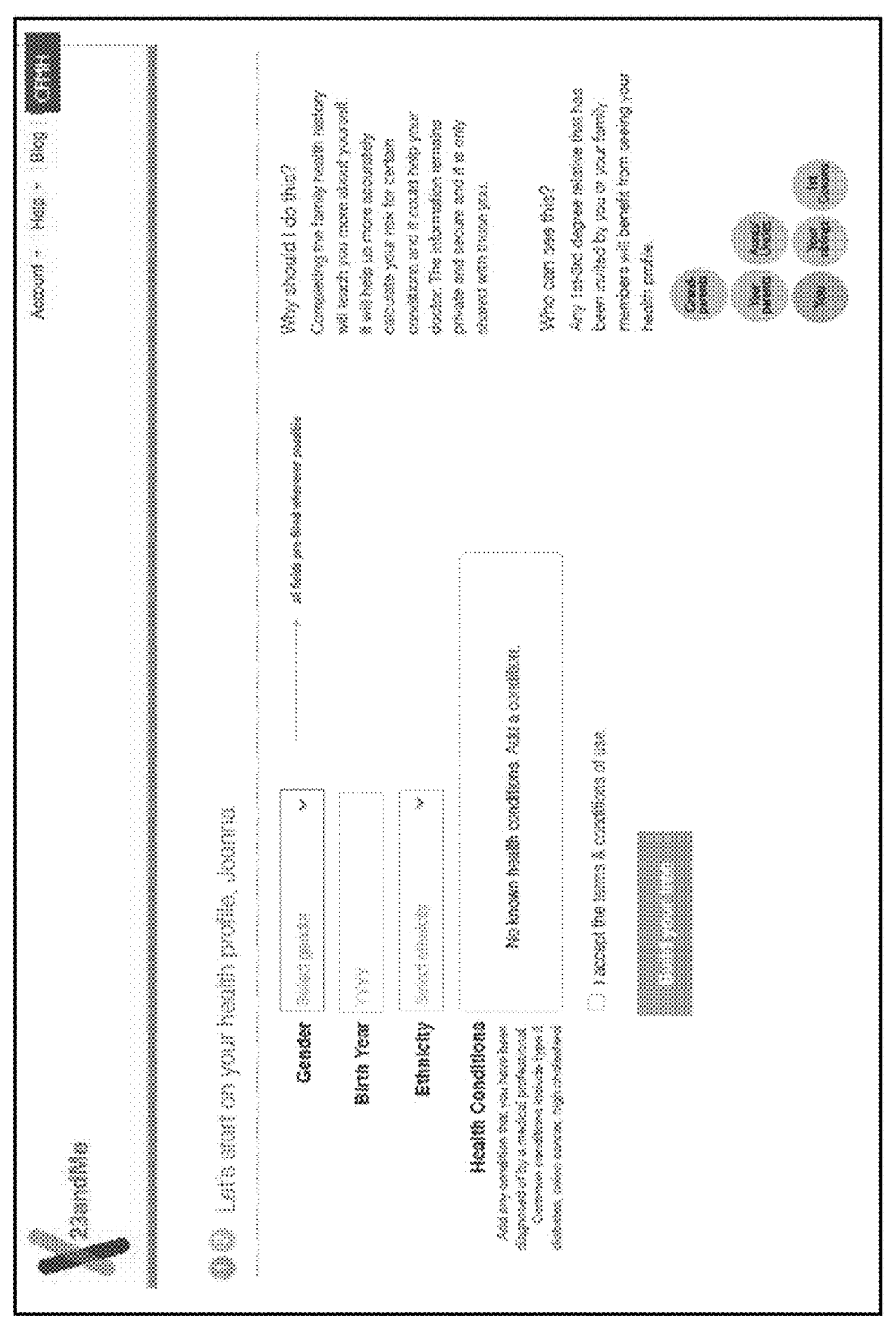
Figure 5B:
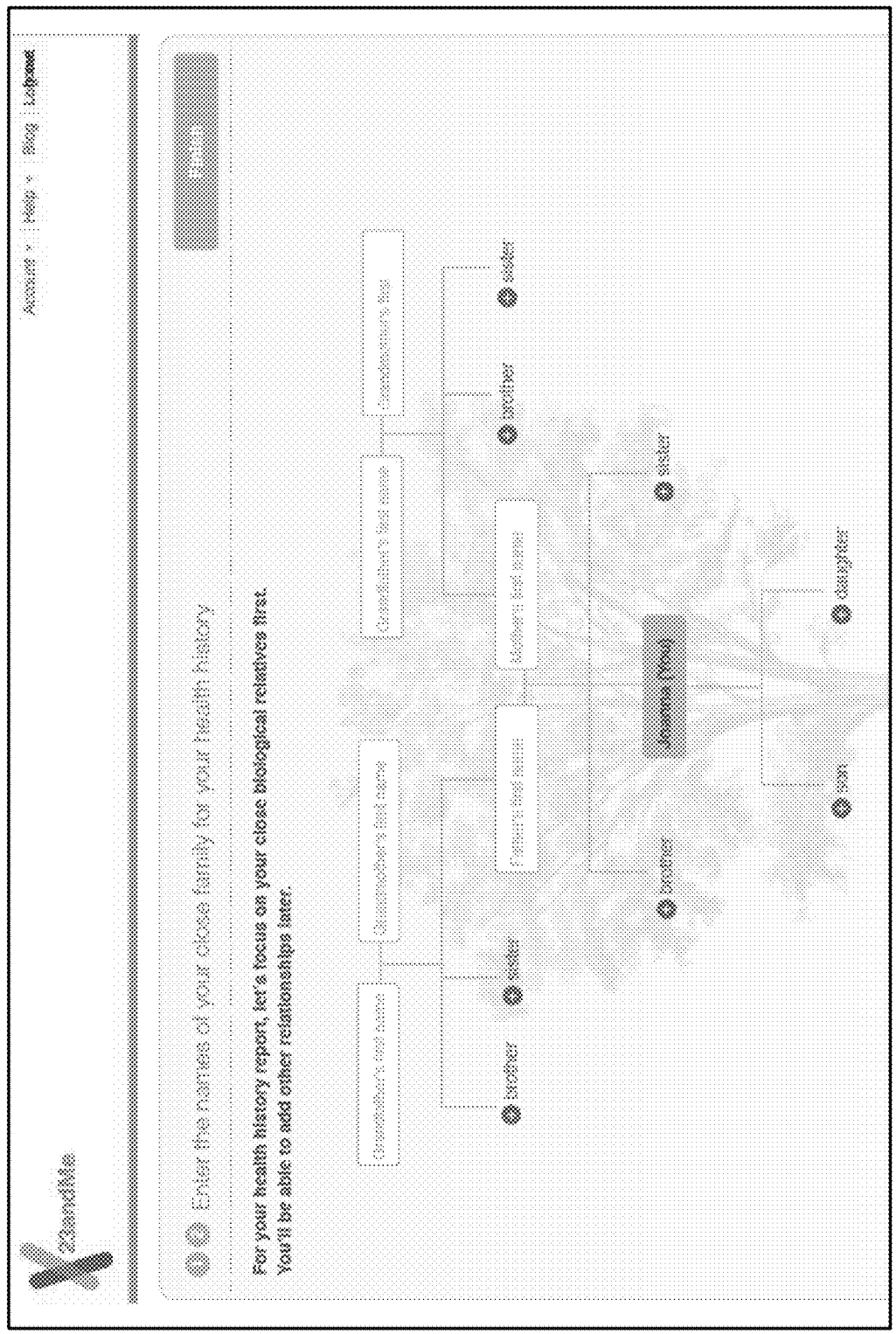
FIG. 5B is a diagram illustrating an embodiment of a family tree template where information is added by one or more users collaborating on the family tree.

In some embodiments, establishing a family tree includes establishing the structure/topology of the family tree. The family tree may include a plurality of nodes, with each node corresponding to a family member, where the nodes are arranged in a tree structure representing family relationships. Genealogical data and family relationships may also be represented in other formats/representations, such as a pedigree or ancestor chart. FIG. 5B provides an example of a family tree.

In some embodiments, an initial user is prompted to generate a family tree. In response to receiving an indication that the user would like to build a family tree, the system presents to the user an initial template family tree that includes an initial predefined set of family member nodes (e.g., parent/grandparent nodes associated with the user). The initial template family tree can be of an initial size, for example, displaying up to $3^{rd}$ degree relatives. The user is prompted to add nodes to the tree (e.g., populating the tree), such as nodes corresponding to brothers, sisters, aunts, uncles, cousins, nieces, nephews, sons, daughters, etc.

The initial user is also prompted to edit/annotate the nodes of the family tree by entering information about the family members/relatives. In various embodiments, editable information includes the name of a family member, the age of the family member, ethnicity, date of birth, date of death (if deceased), blood relation (e.g., stepchild/stepparent, adopted brother, etc.), family history information (e.g., disease history information), environmental information (e.g., smoking habits, diet, exposure to toxins, etc.), as well as phenotype data (e.g., other concurrent diseases/conditions), age of diagnosis of conditions, genetic information, information associated with drug side-effects (e.g., allergies to certain medications), etc. Genetic information, family history information, and/or environmental information may also be retrieved from one or more external databases/storage units such as patient medical records. In various embodiments, the user may edit/annotate information by interacting with editable fields, selecting information from a list or dropdown menu, search querying a database via a search prompt, or via any other appropriate user interaction interface.

In some embodiments, prior to establishing the initial family tree, the initial user building the tree may be prompted to enter information about themselves (e.g., by filling out a questionnaire/survey) or create a health profile (e.g., as shown in FIG. 5A). In various embodiments, the information that the user may be prompted to enter includes, gender, birth year, ethnicity, any known health conditions, as well as any of the editable information described above, etc. In some embodiments, the initial template family tree is constructed/established relative to the initial user (e.g., nodes of parents included in initial template family tree are parents of the initial user). The initial user's information can also include personal genetic information (e.g., sequenced/genotyped information, inferred genetic information, etc.) stored in an internal storage unit (e.g., database 214), or retrieved from one or more external databases/storage units.

In some embodiments, the user may also specify who may see their personal health profile. In some embodiments, viewing of the user's personal health profile may be limited by degree of the invited relatives (e.g., only $1^{st}$-$3^{rd}$ degree relatives that have been invited may view the user's health profile).

In some embodiments, the family tree may be automatically populated based on collected information. For example, if the initial user is a subscriber of the personal genetics services platform and has previously been sequenced/genotyped, IBD or any other appropriate form of analysis may be used to identify or determine whether other subscribers of the service platform may be related to the initial user.

Figure 6:
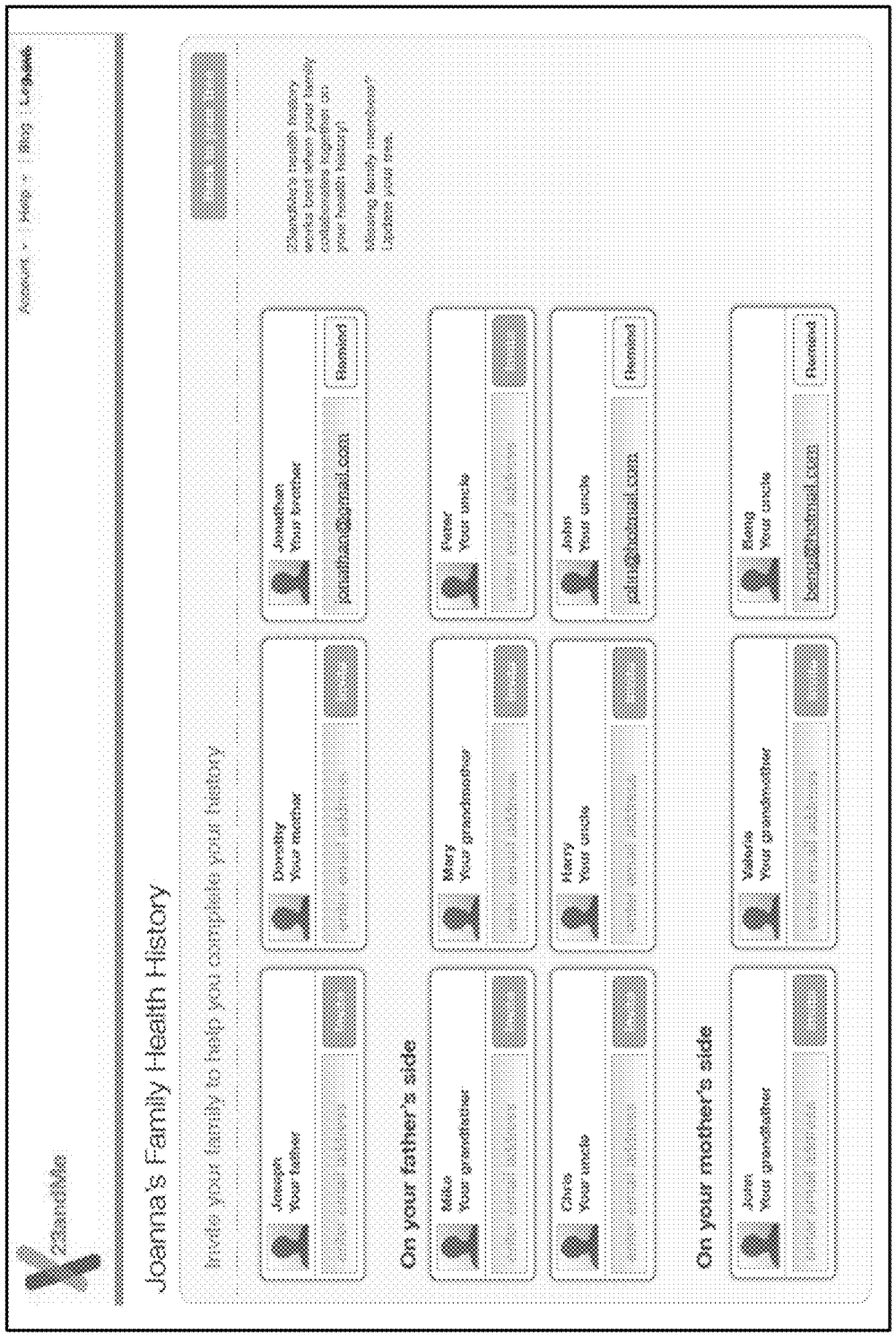
FIG. 6 is a diagram illustrating an embodiment of a user interface for inviting other users to collaborate on the collaborative family medical history (CFMH).

At 404, other users are invited to collaborate on the family medical history and form a more complete view of the tree. In some embodiments, as the family tree is populated by a user, or in response to adding a node in the tree, the user is prompted to invite the family members added to the family tree. As shown in FIG. 6, the user may be prompted to enter the email addresses of various family members. The family members may be organized or otherwise arranged in a user interface by which side of the family tree they are on relative to the user (e.g., paternal/maternal side). In some embodiments, the user is not prompted to invite family members who are indicated to be deceased. Any other appropriate form of communication (e.g., through a genetics platform's social network, through messages sent via external social networks (e.g., Facebook®, Twitter®), through an application, SMS, etc.) may be used to send an invitation. In some embodiments, the invited subscribers are also prompted to create personal profiles as described above.

In some embodiments, suggestions for family members to be invited may be generated based on genetic information. For example, if the user is a subscriber of the personal genetics services platform and has previously been sequenced/genotyped, IBD or any other appropriate form of analysis may be used to identify and determine whether other subscribers of the service platform (or whose genetic information is part of an accessible external database or platform) are related to the user. Specifically, the user's genetic information is compared with the genetic information of other users. If the amount of DNA segments and/or IBD regions between the user and another user exceeds a certain threshold, the other user is deemed to be a potential relative of this user. The determined potential relatives are provided as suggested relatives to the user, who may choose to contact these potential relatives and invite them to collaborate on the family tree.

In some embodiments, merging of family trees is performed. For example, unbeknownst to each other, separate users who are related to each other may be establishing individual trees. However, the trees may be merged in the event that it is determined that the two trees include overlapping nodes (or conflicting data that the two users may wish to collaborate on and resolve) or in the event that one user invites the other user to collaborate on their tree. In some embodiments, merging trees includes verification of the merging. For example, the users of the trees may be prompted to confirm or verify that the merging of an overlapping node is valid (e.g., information about family members is correct, that there are no data conflicts, etc.).

At 406, the family tree is collaborated on by at least some of the family members. In some embodiments, some or all of the family members collaborate by entering information associated with family medical history as described above, for example, by annotating the family tree (e.g., adding nodes, editing information associated with family members, etc.). In some embodiments, a user is allowed to edit/annotate not only their own information, but the information of any relative in the CFMH as well.

In some embodiments, when a user logs into a website to collaborate on the family tree, the tree they are editing is presented from the perspective of the user.

In some embodiments, locking of data is implemented such that two users do not modify the same data simultaneously. In some embodiments group chat functionality is included in a user interface to facilitate discussion among family members (e.g., about potential annotations and edits to the family tree). In some embodiments, collaboration rules/criteria are configured. In various embodiments, collaboration rules include authorization rules on who may edit certain nodes of the collective family history (e.g., by degree of relative where one is only permitted to edit information within three degrees of relatedness or less), what data is editable, etc.

FIG. 5A is a diagram illustrating an embodiment of an initial user interface display for starting a user's health profile. In this example, a user is asked to enter basic health profile information such as gender, birth year, ethnicity, and health conditions. Any $1^{st}$-$3^{rd}$ degree relative that has been invited by the user or by another $1^{st}$-$3^{rd}$ degree relative may be allowed to view the user's health profile. Relatives of higher degrees may also be invited and/or allowed to view the user's health profile. The relatives may also include non-blood related relatives (e.g., aunt who married into the family). As used herein, 'degree' refers to the number of biological links connecting a given pair of individuals. Relatives within third degree include but are not limited to parents, children, siblings, half-siblings, uncles, aunts, nephews, nieces, grandparents, grandchildren, great-grandparents, great-grandchildren, great-uncle, great-aunt, great-nephew, great-niece, and first cousin. A pair of relatives within three degrees is expected to share at least 12.5% of their autosomal DNA, assuming no population consanguinity.

FIG. 5B is a diagram illustrating an embodiment of a family tree template where information is added by one or more users collaborating on the family tree.

FIG. 6 is a diagram illustrating an embodiment of a user interface for inviting other users to collaborate on the collaborative family medical history (CFMH). In the example shown, the user has the option to add relatives to the family tree and invite the relatives to help complete the family medical history tree via email.

Figure 7:
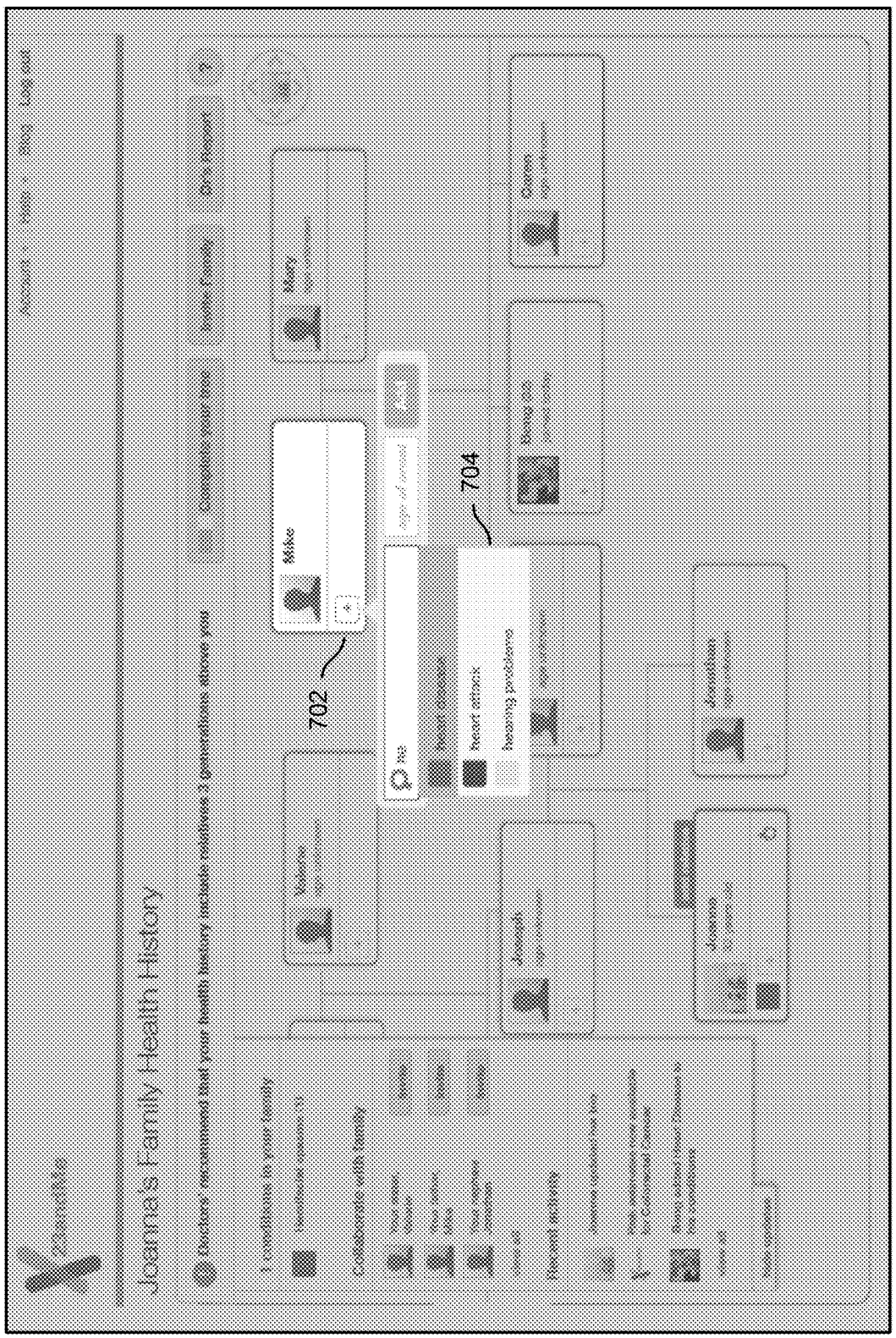
FIG. 7 is a diagram illustrating an embodiment of a user interface used to add medical conditions for family members in the tree.

FIG. 7 is a diagram illustrating an embodiment of a user interface used to add medical conditions for family members in the tree. In the example shown, one or more users collaborating on the family medical history may edit the information associated with a family member in the collective family history. For example, by clicking on the "+" symbol (702), users can view (704) health conditions to associate with a family member named "Mike." Any health conditions that are entered for Mike, by the user or anyone who has been invited to edit the family tree, are displayed. In various embodiments, the user may edit/annotate information by interacting with editable fields, selecting information from a list or dropdown menu, search box for querying a database, or via any other appropriate input interaction.

Figure 8:
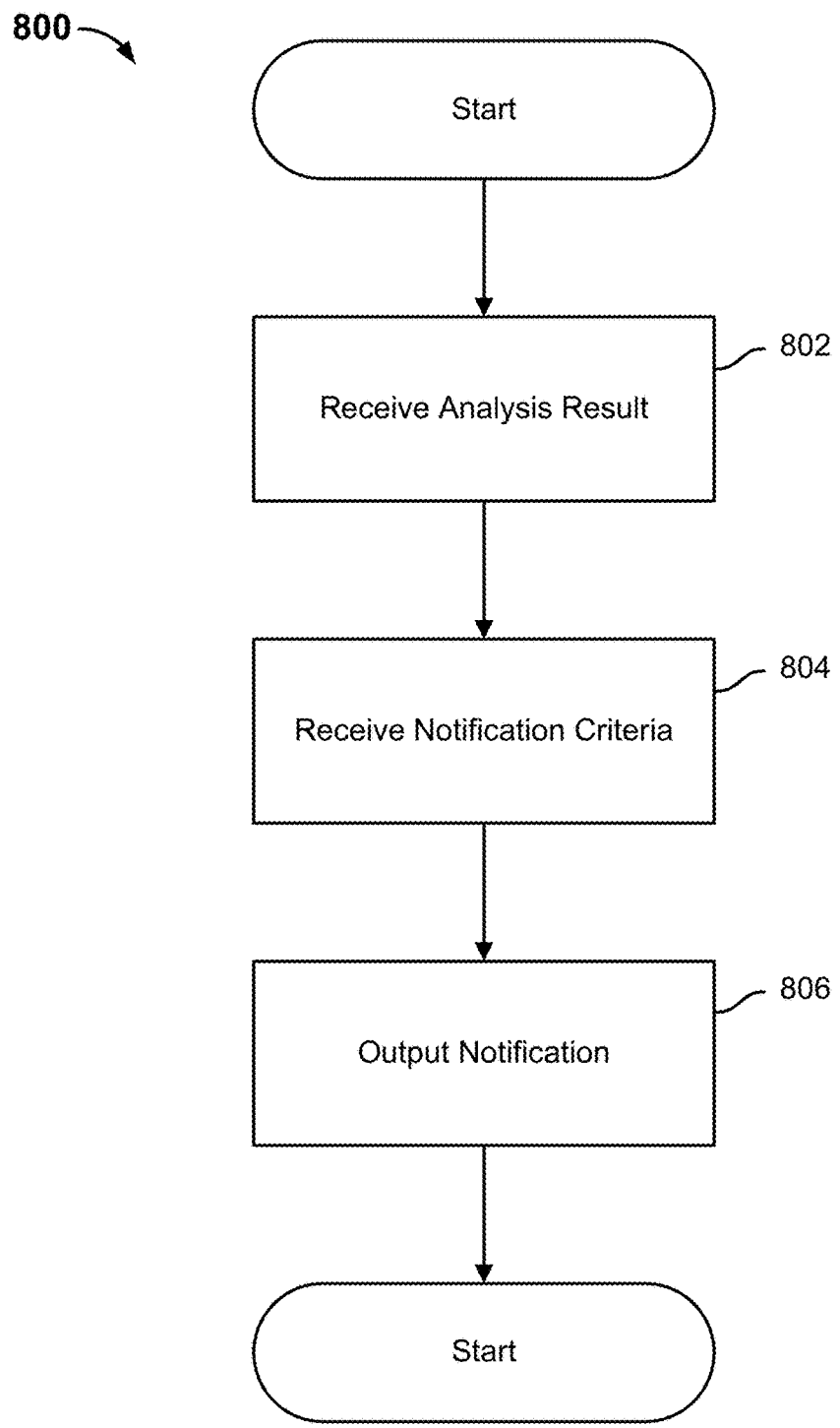
FIG. 8 is a flow diagram illustrating an embodiment of a process for outputting a notification/alert.

FIG. 8 is a flow diagram illustrating an embodiment of a process for outputting a notification/alert. In some embodiments, process 800 of FIG. 8 is used to implement process step 306 of FIG. 3. In some embodiments, process 800 is executed by notification engine 212 of FIG. 2. The process begins at 802, when an analysis result is received. In some embodiments, the analysis result is received from analysis engine 210 of FIG. 2. In some embodiments, the analysis result comprises an estimated risk assessment for a disease condition, and a notification comprising the analysis result is outputted/provided to one or more family members associated with the CFMH.

At 804, notification criteria are received. In some embodiments, notification criteria include default and customizable rules for sending notifications to users of the CFMH. Notifications may be provided to users based on a determination that a notification criteria has been met. In various embodiments, notification criteria include criteria associated with a risk assessment, study participation criteria, recommendation criteria, alert criteria, etc.

At 806, notifications are outputted/provided to some or all of the family members. In some embodiments, notifications are outputted based at least in part on notification criteria and/or received analysis results.

For example, a user may be notified in the event that their risk for a disease condition has changed or when their risk for a disease condition meets or exceeds a threshold. For example, a user may be notified in the event that their risk for a disease condition has met or exceeded a threshold (e.g., the user is placed in a specific risk bucket, or the percentage risk computed for the user exceeds a threshold value, etc.) based on the performed analysis. In addition to the notification of increased risk, the user may also be provided further information about the disease condition (e.g., hyperlinks to medical reference sites), as well as recommendations/suggestions on what they can do to minimize their risk.

In some embodiments, the user/family member may also be notified in the event that their risk for a disease condition has decreased, and further recommendations may be provided on what more the user/family member can do to lower their risk. A user may also be notified in the event that, despite a change in the family medical history, their risk of a disease condition has not increased (e.g., a cousin is diagnosed with breast cancer and found to have a BRCA mutation, but the user does not have IBD with the cousin in the region of the BRCA gene).

In some embodiments, a suggestion notification comprises a recommendation to perform genetic testing. The suggestion notification may be provided based on the annotation of the family medical history as well as risk assessment analysis. For example, if the collective family history indicated that both a user's mother and grandmother had breast cancer, the user may be provided a recommendation to perform genetic testing such as genotyping/sequencing to determine whether they have a genetic mutation (e.g., a BRCA mutation) that may impact their risk of having the disease.

In some embodiments, a notification may be provided based on a comparison of a first family's history against the history of other similar families to identify conditions that are familial but not genetic. For example, it may be determined through analysis that a first family's risk of migraines due to genetic factors is similar to that of other families (e.g., members of the first family do not have alleles for genes that are linked to migraines). Thus, the high incidence of migraines within members of the first family that live in the same household may implicate environmental factors (e.g., radon exposure) as a potential cause of the migraines. Members in the first family that report migraines are notified of this conclusion so they may investigate and/or take corrective measures.

In some embodiments, notifications may be provided in the event that a change has been made to the CFMH. For example, family members may be notified of a new node having been added to the collective family history and may be invited to annotate/edit the new node. In some embodiments, family members are notified when a new risk estimate is available (e.g., in response to a change in the CFMH).

As another example, family members may be notified in the event that they meet study participation criteria. For example, in the event that it is determined that a person of a certain age has a certain disease condition, the person may be notified that they are eligible to participate in a study (e.g., study concerning type II diabetes in children under the age of 12). Families that meet certain study participation criteria (e.g., have a particular allele of a gene) may also be notified. In some embodiments, the services platform keeps track of the frequency with which users annotate and participate in the CFMH, and a user may be notified to participate in a study based on the frequency with which they update the CFMH since frequent updates indicate that the user is interested and possibly more receptive to participating in research studies. For example, if a user updates her CFMH at least once a week, then she may be invited to participate in more studies than users who update their CFMH less than once a month.

In some embodiments, a notification is provided to alert family members that there is missing data still to be entered (e.g., date of birth, disease conditions, health risks, environmental information, age, etc.).

In various embodiments, notifications may be sent as emails to the various family members, may be displayed in the form of a ticker in a user interface displayed to the user when they log on to view the CFMH, may be presented to the user in a pop-up window of a user interface, or via any other appropriate form of notification.

Figure 9A:
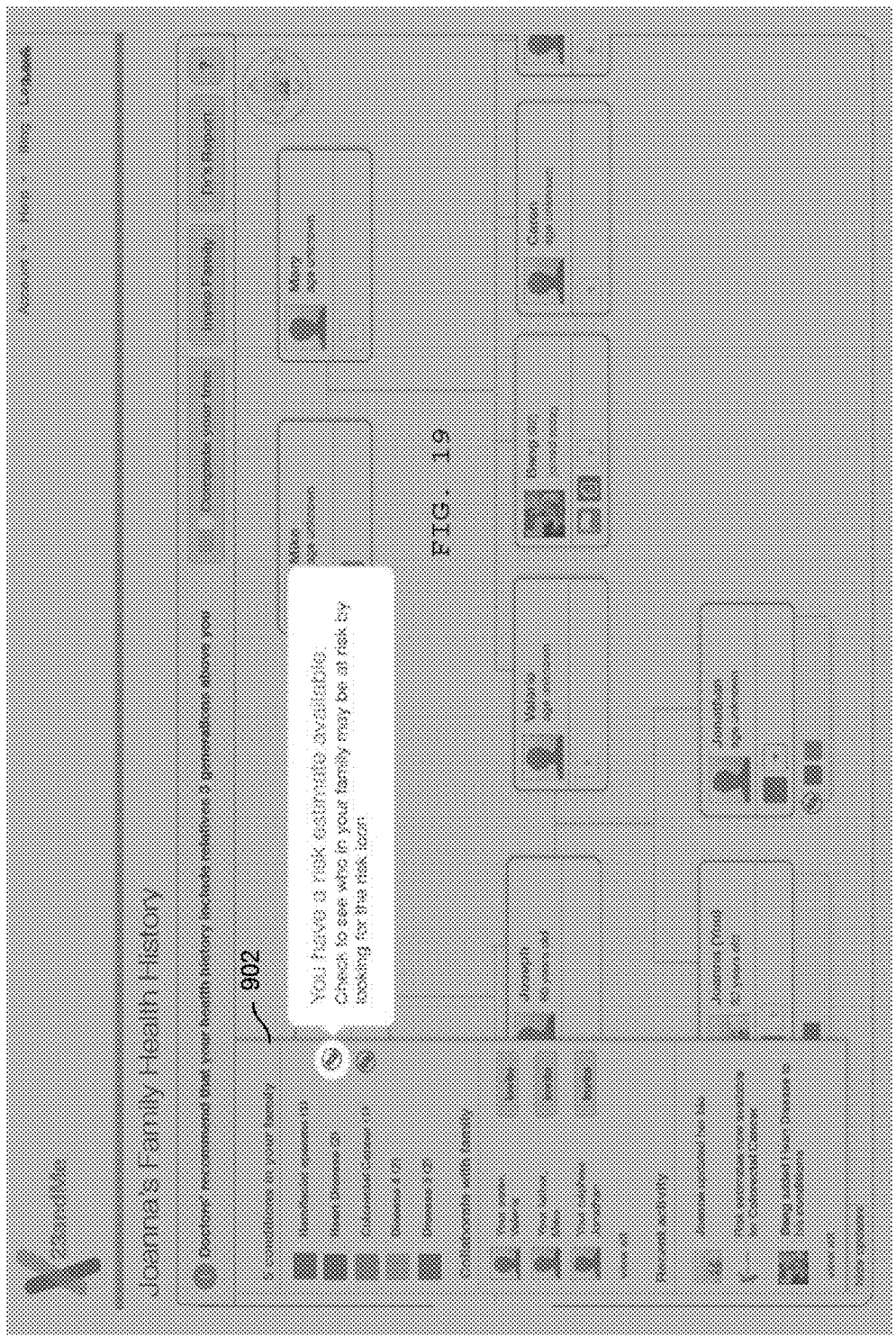
FIG. 9A is a diagram illustrating an embodiment of a user interface used to display disease risk estimates based on information obtained from the CFMH tree and genetic information.

FIG. 9A is a diagram illustrating an embodiment of a user interface used to display disease risk estimates based on information obtained from the CFMH tree and genetic information. In the example shown, multiple medical conditions in the family are identified and collectively presented to the user in a "conditions in your family" area (902). The user can select the condition to determine who in the family has the selected condition. In some embodiments, a visual distinction is made between facts (e.g., date of birth/death, condition that a person is diagnosed with), and estimates (e.g., estimated disease condition risk).

Figure 9B:
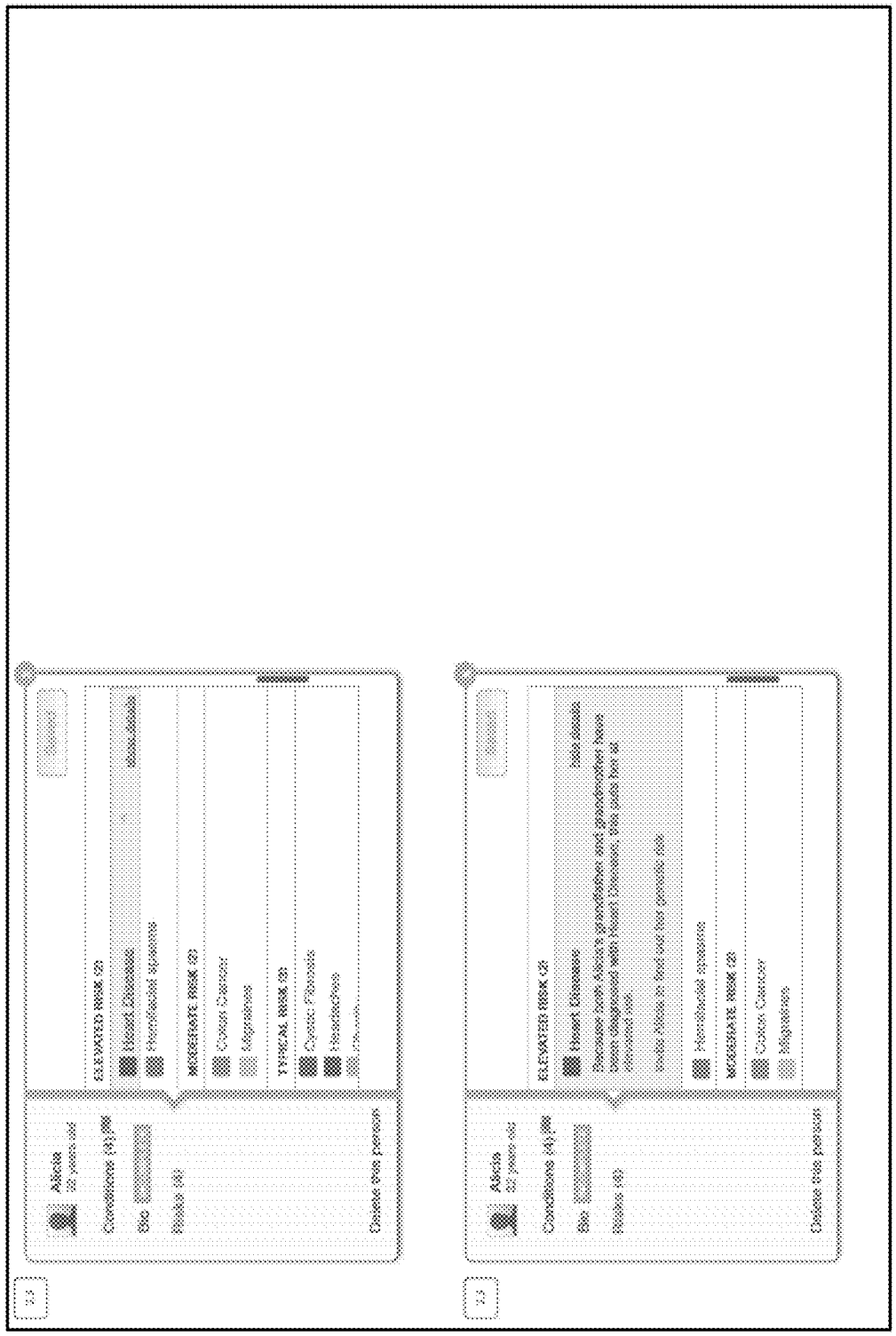
FIG. 9B is a diagram illustrating an embodiment of an interface used to display estimated risk levels.

FIG. 9B is a diagram illustrating an embodiment of an interface used to display estimated risk levels. In this example, a risk is classified as elevated risk, moderate risk, or typical risk. Diseases within each risk category are listed. The user can select the disease and see the reason for the disease risk. For example, a user Alicia can see that she is at elevated risk for heart disease because both her grandfather and grandmother have been diagnosed with heart disease.

Figure 10:
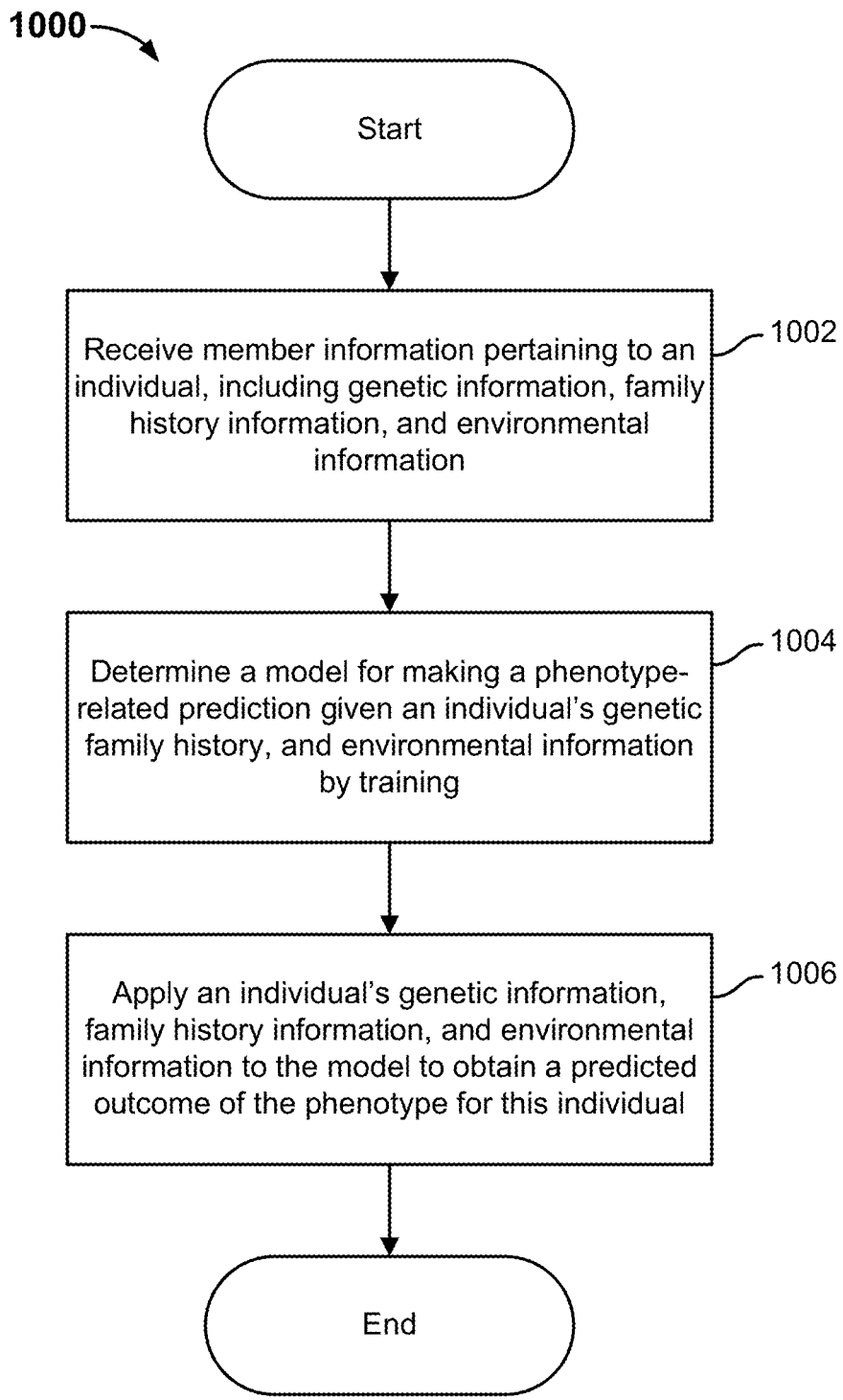
FIG. 10 is a flowchart illustrating an embodiment of a process for making model-based phenotype predictions.
Figure 12:
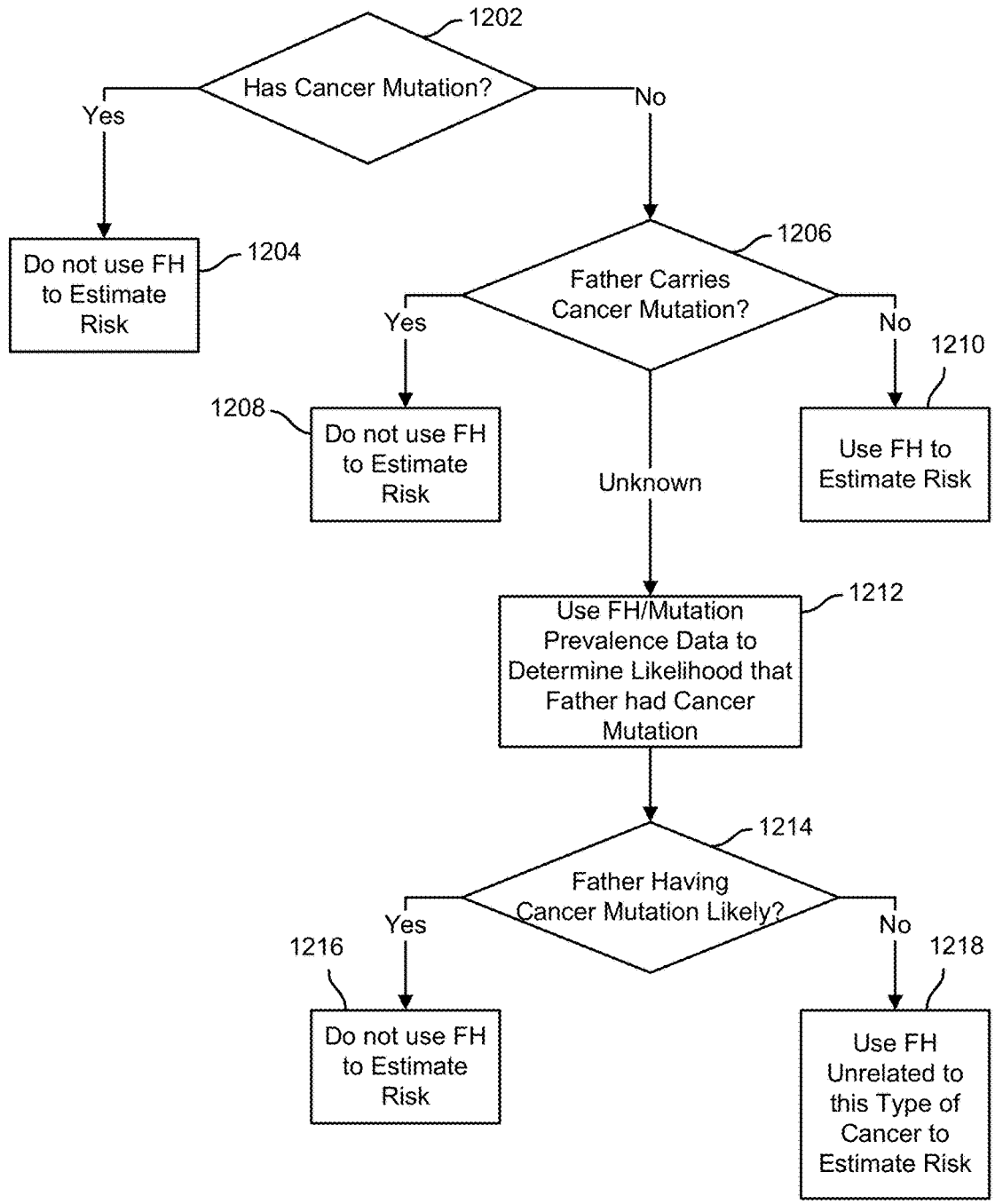
FIG. 12 is an example of a simplified, manually constructed decision tree that uses expert rules to approximately account for the correlation between the status of certain deleterious and highly penetrant genes that are highly correlated with a specific type of disease, and family history.
Figure 13:
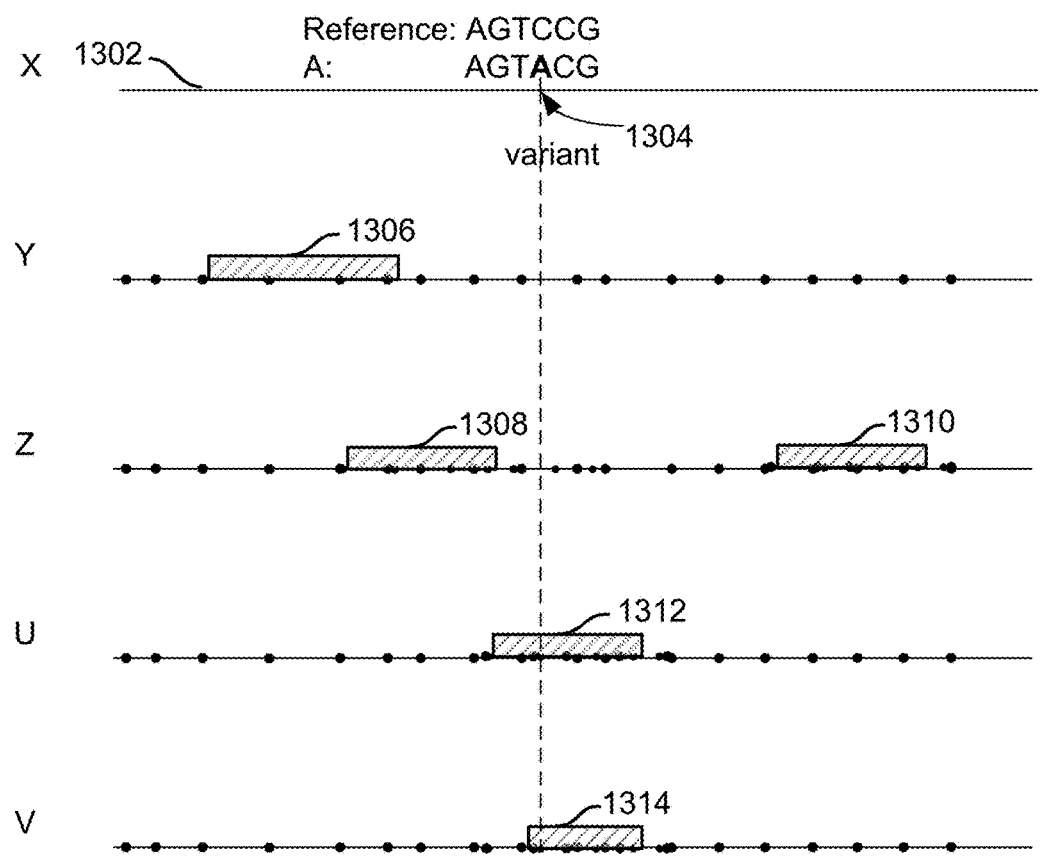
FIG. 13 is a diagram illustrating an example of determining IBD between individuals.

Referring again to 304 of FIG. 3, several techniques for analyzing the CFMH information are described in greater detail herein. FIGS. 10-12 describe a model-based analysis technique for phenotype prediction. FIG. 13 illustrates an IBD-based analysis technique. Other techniques can be used.

FIG. 10 is a flowchart illustrating an embodiment of a process for making model-based phenotype predictions. Process 1000 may be implemented on a system such as 200. The process uses the information of an individual and a statistically significant number of members of a personal genetics services platform (e.g., platform 206) to build and optionally validate a model for phenotype prediction.

At 1002, information pertaining to an individual is received. The information associated with the individual includes genetic information, family history information (e.g., CFMH information), and environmental information of the individual. The genetic information, family history information, and/or environmental information may also be retrieved from one or more external databases such as patient medical records.

At 1004, a model is determined for making a phenotype-related prediction given an individual's genetic, family history, and environmental information. In some embodiments, modeling techniques (e.g., machine learning techniques such as regularized logistic regression, decision tree, support vector machine, etc.) are applied to all or some of the member information to train a model for predicting the likelihood associated with a phenotype such as a disease as well as the likelihood of having a non-disease related genotype such as eye color, height, etc. In some embodiments, the models are derived based on parameters published in scientific literature and/or a combination of literature and learned parameters. As will be described in greater detail below, in some embodiments, the model will account for, among other things, genetic inheritance and any known relationships between genetic information and the phenotype.

At 1006, an individual's genetic information, family history information, and environmental information is applied to the model to obtain a predicted outcome of the phenotype for this individual. In some embodiments, the predicted outcome is age dependent. In other words, the predicted outcome indicates how likely the individual may have a particular disease by a certain age/age range.

An embodiment of a process for determining a model is described in an example below. For purposes of illustration, the phenotype of interest in the example is Parkinson's disease (PD), although models may be derived for risk prediction of many other phenotypes.

FIG. 11 is a diagram illustrating an embodiment of a member information table used to train and validate the model. In this example, member information with respect to Parkinson's disease is kept in the table, where each row corresponds to the information of a member, and each column corresponds to a particular piece of information. Multiple columns are grouped to correspond to genetic information, family history information, environmental information, etc. The genetic information includes whether the member possesses risk alleles (an allele of a genetic polymorphism associated with an increased risk for PD) in SNPs found to be independently associated with PD; the family history information includes answers to survey questions such as whether the mother or father has PD; and the environmental information includes answers to survey questions such as whether the member has had pesticide exposure at work. In addition, the table stores the members' PD status and optionally personal information, such as age, geographical location, etc.

In some embodiments, a logistic regression technique is used to determine the model. In this example, a subset of the rows (e.g., member data for members 1-3000) is selected as training data and the remaining rows (e.g., member data for members 3001-4000) are used for validation.

In one example where logistic regression is performed, for each row of the table, the genetic and environmental information is encoded as a multidimensional vector. Many possible encoding techniques exist. One example of a specific encoding technique is to include the number of copies of risk alleles for each SNP (0, 1, or 2) as separate entries in the vector, the presence or absence of PD in any relative (0=no, 1=yes), and the presence or absence of various environmental factors (0=no, 1=yes, per environmental factor); we refer to each of the elements of the vector as "features." For notational convenience, we denote the multidimensional vector for the i-th row of the table as $x^{(i)}=(x_{i,1}, x_{i,2}, \ldots, x_{i,n})$. Here, n represents the number of encoded features, and $x_{i,j}$ represents the j-th encoded feature for the i-th example. Let m denote the number of examples in the training set, and let $y=(y^{(1)}, y^{(2)}, \ldots, y^{(m)})$ denote an encoding of the phenotypes for each individual in the training set ($y^{(i)}=1$ indicates that the i-th individual reported developing the disease, whereas $y^{(i)}=0$ indicates that the i-th individual did not report developing the disease).

In the logistic regression example, we consider a model of the form $$P(y=1|x;w,b)=1/(1+\exp(-w^T x-b)) \quad (1).$$

Here, x corresponds to an n-dimensional vector of encoded features, and y is the encoded phenotype. The parameters of the model include b (a real-valued intercept term) and $w=(w_1, w_2, \ldots, w_n)$ (an n-dimensional vector of real-values). The notation $w^T x$ is taken to mean the dot product of the vectors w and x (i.e., $\Sigma_{j=1,\ldots,n} w_j x_j$). The expj( ) operator refers to exponentiation base e. As specified above, for any vector x, the logistic regression model outputs a value between 0 and 1 indicating the probability that an individual with encoded features x will report having developed the phenotype such as a disease (i.e., y=1).

In the logistic regression example, the parameters of the model (w and b) are chosen to maximize the logarithm (base e) of the regularized likelihood of the data; this quantity, known as the regularized log-likelihood, is specified as follows:

$$L(w,b)=\Sigma_{j=1,\ldots,m} \log P(y^{(i)}|x^{(i)};w,b)-0.5Cw^T w \quad (2).$$

Here, C is a real-valued hyperparameter that is chosen via cross-validation (as described below). The first term of the objective function is a log-likelihood term that ensures that the parameters are a good fit to the training data. The second term of the objective (i.e., $0.5\ w^T w$) is a regularization penalty that helps to ensure that the model does not overfit. The hyperparameter C controls the trade-off between the two terms, so as to ensure that the predictions made by the learned model will generalize properly on unseen data.

In the logistic regression example, a cross-validation procedure is used to select the value of the hyperparameter C. In this procedure, we fit the parameters of the model (w and b) by maximizing the objective function specified in equation (1) for multiple values of C (e.g., . . . ⅛, ¼, ½, 1, 2, 4, 8, . . . ) using data from the training set (e.g., member data for members 1-3000). For each distinct value of C, we obtain a parameter set, which we then evaluate using a validation objective function based on the validation set (e.g., member data for members 3001-4000). The parameters (and corresponding value of C) which achieve the highest validation objective function are returned as the optimal parameters (and hyperparameter) for the model. For this example, a reasonable validation objective function is the following:

$$L'(w,b)=\Sigma_{i=m+1,\ldots,M} \log P(y^{(i)}|x^{(i)};w,b) \quad (3).$$

Here, $x^{(m+1)}$ through $x^{(M)}$ correspond to the multidimensional vectors of features for the validation data. Note that the validation objective function does not include a regularization term, unlike the objective function (2).

In some embodiments, the data set is divided into several portions, and training and validation are repeated several times using selected combinations of the portions as the training sets or validation sets. For example, the same set of information for 4000 members may be divided into 4 portions of 1000 members each, and training/validation may be repeated 4 times, each time using a different set of member information for 1000 members as the validation set and the rest of the member information as the training set.

In some embodiments, a decision tree is generated as the model for predicting a phenotype such as PD. A decision tree model for predicting outcomes associated with a genotype can be created from a matrix of genotypic, family history, environmental, and outcome data. The member information example shown in FIG. 11 can also be used to generate the decision tree. The model can be generated with a variety of techniques, including ID3 or C4.5. For example, using the ID3 technique, the tree is iteratively constructed in a top-down fashion. Each iteration creates a new decision junction based on the parameter that results in the greatest information gain, where information gain measures how well a given attribute separates training examples into targeted classes. In other cases, the structure of the decision tree may be partially or completely specified based on manually created rules in situations where an automated learning technique is infeasible In some embodiments, the decision tree model is validated in the same way as the logistic regression model, by training and evaluating the model (retrospectively or prospectively) with a training set of individuals (e.g., members 1-3000) and an independent validation set (e.g., members 3001-4000).

In some embodiments, the model determination process accounts for genetic inheritance and the correlation of genetic information with family history information. There are various cancer studies showing that certain mutated genes are inherited according to Mendelian principles and people with mutations in these genes are known to be at significantly higher risk for certain types of disease (such as familial prostate cancer, breast cancer, etc.). In other words, possession of such mutated genes and having family members that have the disease are highly correlated events. The model, therefore, should account for such correlation.

FIG. 12 is an example of a simplified, manually constructed decision tree that uses expert rules to approximately account for the correlation between the status of certain deleterious and highly penetrant genes that are highly correlated with a specific type of disease, and family history. The techniques described herein are generally applicable to various types of highly penetrant genetic mutations linked to certain diseases. For purposes of example, it is assumed that the mutated gene is highly correlated with a specific type of cancer that commonly occurs in men (e.g., prostate cancer). In this embodiment, the status of the specific deleterious mutations (also referred to as the cancer mutations) is used to determine whether to use the member's family history, in particular, the history of having the specific type of cancer on the father's side, to predict the member's risk of developing the specific type of cancer. A primary assumption of this simplified model is that the specific type of cancer risk is modified by known deleterious mutations and by a large set of unknown mutations in other genes. The cancer mutations may be assayed directly using a genotyping technology. The influence of unknown mutations can only be indirectly measured by measuring family history for the disease. In more sophisticated models, the presence of common, low-penetrance mutations would also be included in the calculation.

At the first level, the tree splits into two branches according to whether the member has been positively tested for deleterious cancer mutations (1202). If the member has a deleterious cancer mutation, his risk for the specific type of cancer (referred to as cancer risk in this example) is significantly increased due to this risk factor. In comparison, family history of whether the member's father had the specific type of cancer is assumed to have minimal additional effect on the member's cancer risk and is therefore not included in estimating the member's risk (1204). This is because if the father had this type of cancer, it is very likely that the father's cancer was caused by the highly penetrant cancer mutation; therefore, this piece of information would not add significantly to the member's already elevated risk. Accordingly, in the simplified model, the father's history of having the specific type of cancer is omitted when the member carries a deleterious cancer mutation. In more complex models, the father's history of having the specific type of cancer may be accounted for even if the member carries a deleterious cancer mutation (e.g., the fact that the father had this type of cancer will increase the member's risk by a small percentage, regardless of whether the member carries a deleterious cancer mutation).

If, however, the member does not carry a deleterious cancer mutation, at the next level of the tree, a determination is made as to whether the member's father carries the cancer mutation (1206). If the father carries the cancer mutation, the father's family history (e.g., the father's brothers also had this type of cancer) is likely to be correlated with the presence of the cancer mutation in the family, which should not significantly affect the member's own cancer risk calculations given that any elevated risk due to the cancer mutation is already ruled out for the member. Thus, additional family history on the father's side is not used to estimate the member's risk (1208).

If, however, the member's father also has no cancer mutation, then the family history should be used to estimate the member's cancer risk (1210), based on the assumption that there may be other risk-modifying genes that are not yet identified but whose influence is detectable indirectly by noting a family history of the disease. In some embodiments, a first-degree relative (e.g., the father) with the disease is thought to increase the member's risk 4-fold, and a second-degree relative (e.g., an uncle) with the disease is thought to increase the member's risk 2-fold. The increase in risk attributable to the presence of disease in a relative can be estimated empirically by collecting data on disease prevalence in related and unrelated individuals.

If the father's cancer mutation status is unknown, family history (e.g., an autosomal dominant inheritance pattern such as multiple siblings having the type of cancer) and/or mutation prevalence data (e.g., the prevalence of the cancer mutations in a particular ethnic group) is used to determine how likely the father is to carry a deleterious cancer mutation (1212). In this simplified model, if it is likely that the father (and therefore the father's side of the family) carries a deleterious cancer mutation, then the model does not further require (or gives less weight to) cancer related family history on the father's side for making the risk prediction (1216), since it is likely that the father's cancer was caused by the cancer mutation and it is already known that the member has not inherited the cancer mutation. If, however, it is unlikely that the father carries the cancer mutation, then the model requires (or gives full weight to) family history unrelated to the specific type of cancer on the father's side to estimate risk (1218), since it tends to reveal the influence of other unidentified risk-modifying genes.

As can be seen from the example above, in a simplified model, when genetic information highly predictive of the phenotype is present (e.g., carrying a deleterious cancer mutation is highly predictive of certain types of cancer), the model does not further require family history information that is correlated with the phenotype (e.g., whether the father carries the deleterious cancer gene) to make the prediction. In some embodiments, more complex models take the correlated family history into consideration for making the prediction, but account for the correlation by giving less weight to the correlated family history information.

A trained and validated model for predicting a phenotype can be used to predict an individual's likelihood of exhibiting the phenotype. In some embodiments, an individual's information (e.g., the individual's genetic, family, and environmental information) is input and applied to the model (e.g., the regression model or the decision tree described above) to derive the predicted result. In some embodiments, the predicted result is compared with a certain threshold. If the predicted result exceeds the threshold, the system may provide the individual with additional feedback or suggestions, such as getting additional testing that more precisely targets the genotype in question and requesting the user to provide additional phenotypic, family, and/or environmental information to improve the prediction, etc. If the individual provides the additional information requested, the prediction process may be re-executed while taking into account the additional information.

FIG. 13 describes a technique for determining IBD regions.

In some embodiments, determining IBD comprises identifying cohorts of individuals who share certain VUS (variants of unknown significance) and interpreting VUS from a sequenced proband (an individual being studied) using a large database of genome data for individuals.

In some embodiments, DNA samples (e.g., saliva samples) are assayed using genotyping chips (such as Illumina HumanHap550v3). Each individual's genomic information is represented using Single Nucleotide Polymorphisms (SNPs)), which are known points along the genome with two or more common variations.

Because of recombination and independent assortments of chromosomes, the autosomal DNA and X chromosome DNA (collectively referred to as recombining DNA) from the parents is shuffled at the next generation, with small amounts of mutation. Thus, only relatives will share long stretches of genome regions where their recombining DNA is completely or nearly identical. Such regions are referred to as "Identical by Descent" (IBD) regions because they arose from the same DNA sequences in an earlier generation. In some embodiments, individuals in the database that share a variant-overlapping IBD region with the proband are identified. A variant-overlapping IBD region is a DNA segment that corresponds to an IBD region, and that overlaps the location where the genetic variant is found.

In FIG. 13, the genome of the proband, X, is represented by line 1302. A particular variant in X's genome is identified at location 1304. In this example, the sequence of a reference genome at this location is "AGTCCG", and the sequence of X's genome is "AGT<u>A</u>CG" (the second A being the variant base). X can be sequenced (fully or in a particular region), or genotyped and in addition have the variant at 1304 specifically identified. Note that the technique of identifying the variant in 1304 need not be the same as assaying the SNP variation used to compute IBD between X and other individuals in the database.

Y, Z, U, and V are other individuals whose genotype information is stored in the database. The actual number of individuals in the database can be much greater. Note that the sequence information of these individuals at location 1304 is not necessarily known since the chips used to assay their DNA samples in this case produce SNPs, the locations of which are represented as dots on the line. The SNPs are present in specific locations of the individuals' genome.

It is determined whether other individuals in the database (such as Y, Z, U, V) have DNA segments overlapping the variant location 1304 that is IBD with respect to X's genome. This can be performed using existing IBD identification techniques such as fastIBD. In this case, although Y shares an IBD region 1306 (shown as shaded box) with X, this region does not overlap the variant location; Z shares IBD regions 1308 and 1310 with X, but neither region overlaps the variant location; U shares IBD region 1312 with X, and this region overlaps the variant location; V shares IBD region 1314 with X, and this region overlaps the variant location. These IBD segments are typically short (e.g., <5 cM) and usually belong to distant relatives who share only one segment with the proband. Since the IBD regions are supposed to be identical between individuals, although the sequence information for location 1304 is not necessarily known for individuals U and V, because they share IBD regions with X that overlap the variant location, it is inferred that U and V would also have the same variant at location 1304 (in this case, "AGTACG"). In this case, U and V are deemed to be matching individuals since they both share variant-overlapping IBD regions with X (and therefore are assumed to have the same genetic variant).

In some embodiments, the genotype and/or phenotype information of the U and V information is output and can be used for a variety of purposes. For example, U and V can be included in a cohort for statistical analysis, testing for phenotypic association with this particular variant, etc. For instance, the technique can be used to test rare mutations (particularly ones that are not present on the genotyping chip and therefore not genotyped) in cancer genes to determine (or validate existing theories on) whether specific mutations are associated with increased odds of getting a particular type of cancer or are benign polymorphisms that are not associated with increased risk of getting that type of cancer.

Preferably, further validation is needed to ensure that the variant is not a private mutation (a mutation present in one person or family), or a de novo mutation (specifically, a new mutation in an individual). In some embodiments, once the cohort is formed, one or more individuals in the cohort may be sequenced to determine that the mutation is not private or de novo. Take the example above, once it is established that U and V are in the cohort, if further assaying of U and V's genes shows that neither has the same variant as X at location 1304, then it is likely that X's variant is private or de novo. If, however, U and/or V have the same variant, then it is unlikely that X's variant is private or de novo.

An example technique for determining IBD regions is described. The standard SNP-based genotyping technology results in genotype calls each having two alleles, one from each half of a chromosome pair. As used herein, a genotype call refers to the identification of the pair of alleles at a particular locus on the chromosome. Genotype calls can be phased or unphased. In phased data, the individual's diploid genotype at a particular locus is resolved into two haplotypes, one for each chromosome. In unphased data, the two alleles are unresolved; in other words, it is uncertain which allele corresponds to which haplotype or chromosome.

The genotype call at a particular SNP location may be a heterozygous call with two different alleles or a homozygous call with two identical alleles. A heterozygous call is represented using two different letters such as AB that correspond to different alleles. Some SNPs are biallelic SNPs with only two possible states for SNPs. Some SNPs have more states, e.g., triallelic. Other representations are possible.

In this example, A is selected to represent an allele with base A and B represents an allele with base G at the SNP location. Other representations are possible. A homozygous call is represented using a pair of identical letters such as AA or BB. The two alleles in a homozygous call are interchangeable because the same allele came from each parent. When two individuals have opposite-homozygous calls at a given SNP location, or, in other words, one person has alleles AA and the other person has alleles BB, it is very likely that the region in which the SNP resides does not have IBD since different alleles came from different ancestors. If, however, the two individuals have compatible calls, that is, both have the same homozygotes (i.e., both people have AA alleles or both have BB alleles), both have heterozygotes (i.e., both people have AB alleles), or one has a heterozygote and the other a homozygote (i.e., one has AB and the other has AA or BB), there is some chance that at least one allele is passed down from the same ancestor and therefore the region in which the SNP resides is IBD. Further, based on statistical computations, if a region has a very low rate of opposite-homozygote occurrence over a substantial distance, it is likely that the individuals inherited the DNA sequence in the region from the same ancestor and the region is therefore deemed to be an IBD region.

An embodiment of a process for determining an IBD region between two individuals is described. First, consecutive opposite-homozygous calls in the users' SNPs are identified. The consecutive opposite-homozygous calls can be identified by serially comparing individual SNPs in the users' SNP sequences or in parallel using bitwise operations. Next, the distance between consecutive opposite-homozygous calls is determined. Next, IBD regions are identified based at least in part on the distance between the opposite-homozygous calls. The distance may be physical distance measured in the number of base pairs or genetic distance accounting for the rate of recombination. For example, in some embodiments, if the genetic distance between the locations of two consecutive opposite-homozygous calls is greater than a threshold of 10 centimorgans (cM), the region between the calls is determined to be an IBD region. This step may be repeated for all the opposite-homozygous calls. A tolerance for genotyping error can be built by allowing some low rate of opposite homozygotes when calculating an IBD segment. In some embodiments, the total number of matching genotype calls is also taken into account when deciding whether the region is IBD. For example, a region may be examined where the distance between consecutive opposite-homozygous calls is just below the 10 cM threshold. If a large enough number of genotype calls within that interval match exactly, the interval is deemed IBD.

While genomic data included the example database described above mainly include genotype data such as SNP data, the techniques described are also applicable to exome data (which comprises exons, the coding portion of genes that are expressed), other assayed DNA marker data (e.g., short tandem repeats (STRs), Copy-Number Variants (CNVs), etc.), sequenced genome data (fully sequenced or in a particular region), as well as any other appropriate form of genetic data.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A computer-implemented method for determining and graphically displaying a potential risk condition of a user using a user interface for a system comprising a computer and one or more databases comprising phenotype data and/or genetic information, the method comprising:
    displaying the user interface on a display device, the user interface comprising:
    a list of potential risk conditions; and
    a family tree template comprising nodes for a plurality of blood relatives of the user and configured for receiving and displaying collaborative family medical history (CFMH) information of the user and at least one of the plurality of blood relatives of the user, each blood relative being a relative who shares at least one common ancestor with the user, wherein the CFMH information includes phenotype data and/or genetic information of the user and at least one of the plurality of blood relatives of the user;
    receiving, from the user via input into a node of the family tree template of the user interface, at least phenotype data for the at least one of the plurality of blood relatives of the user;
    receiving, from the user via input into a position of the user interface, an address for electronic invitation to a first blood relative of the plurality of blood relatives of the user to collaborate on the CFMH information;
    sending an electronic invitation to the first blood relative to invite the first blood relative to collaborate with the user on the CFMH information;
    receiving, from the user via input into a node of the family tree template of the user interface, confirmation or verification that an overlapping node of the family tree template of the user interface and a secondary family tree template of the first blood relative does not have conflicting data;
    based upon CFMH information received from the user and/or the first blood relative, annotating, by a processor of the computer, the family tree template to display the CFMH information for the at least one of the plurality of blood relatives of the user;
    developing, based at least in part on the CFMH information, a machine learning model trained on information comprising phenotype data and genetic information for determining a potential risk condition of the user and/or the at least one relative of the plurality of relatives of the user;
    using the CFMH information, determining the potential risk condition by inputting the CFMH information into the machine learning model trained on information comprising phenotype data and genetic information; and
    displaying on the user interface the potential risk condition of the user and/or the potential risk condition of the at least one of the plurality of blood relatives of the user.

2. A computer-implemented method for determining and graphically displaying a potential risk condition of a user using a user interface, the method comprising:
    displaying the user interface on a display device, the user interface comprising:
    a list of potential risk conditions; and
    a family tree template comprising nodes for a plurality of relatives of the user and configured for receiving and displaying collaborative family medical history (CFMH) information of the user and at least one relative of the plurality of relatives of the user, wherein the CFMH information includes phenotype data and/or genetic information of the user and at least one of the plurality of relatives of the user;
    receiving, from the user, CFMH information for at least one relative of the plurality of relatives of the user;
    receiving from the user an address for electronic invitation to a relative to collaborate on the CFMH information;
    based upon CFMH information received from the user and/or the at least one relative of the plurality of relatives, annotating, by a processor of the computer, the family tree template to display the CFMH information for the at least one relative of the plurality of relatives of the user;
    developing, based at least in part on the CFMH information, a machine learning model trained on information comprising phenotype data and genetic information for determining a potential risk condition of the user and/or the at least one relative of the plurality of relatives of the user;
    using the CFMH, determining the potential risk condition by inputting the CFMH information into the machine learning model trained on information comprising phenotype data and genetic information; and displaying on the user interface the potential risk condition of the user and/or the potential risk condition of the at least one of the plurality of relatives of the user.

3. The method of claim 2, wherein the CFMH information is stored in one or more databases.

4. The method of claim 2, wherein the CFMH information includes a disease condition of at least one of the plurality of relatives.

5. The method of claim 2, wherein the CFMH information includes genetic information of at least one of the plurality of relatives.

6. The method of claim 2, wherein the CFMH information includes information associated with drug side-effects.

7. The method of claim 2, wherein the genetic information includes genotype information.

8. The method of claim 2, wherein the genetic information includes genetic sequence information and inference based on the genetic sequence information and Identical by Descent (IBD) regions shared by the user and at least one of the plurality of relatives.

9. The method of claim 2, wherein the CFMH information includes one or more environmental factors.

10. The method of claim 2, further comprising sending a notification in the event that the potential risk condition meets criteria.

11. The method of claim 10, wherein the criteria comprise the potential risk exceeds a threshold.

12. The method of claim 2, further comprising determining that the user, at least one of the plurality of relatives of the user, or both, meet criteria for a study.

13. The method of claim 2, further comprising comparing the CFMH information of the user with the CFMH information of another family, and determining a condition that is familial but non-genetic.

14. The method of claim 2, wherein presenting to the user the potential risk condition of the user and/or the potential risk condition of the at least one of the plurality of relatives of the user includes annotating or editing the list of potential risk conditions.

15. The method of claim 2, further comprising displaying on the user interface an editable field, dropdown menu, or search box for querying a database.

16. The method of claim 2, further comprising sending a notification of changes made to the CFMH information.

17. The method of claim 2, further comprising displaying on the user interface a reason for the potential risk condition.

18. The method of claim 2, wherein each relative shares at least one common ancestor with the user.

19. The method of claim 2, further comprising receiving, from the user via prompts displayed on the user interface, CFMH information of the user.

* * * * *